US007105352B2

(12) United States Patent
Asher et al.

(10) Patent No.: US 7,105,352 B2
(45) Date of Patent: *Sep. 12, 2006

(54) INTELLIGENT POLYMERIZED CRYSTALLINE COLLOIDAL ARRAY CARBOHYDRATE SENSORS

(75) Inventors: Sanford A. Asher, Pittsburgh, PA (US); Vladimir L. Alexeev, Pittsburgh, PA (US); Igor K. Lednev, Pittsburgh, PA (US); Anjal C. Sharma, Pittsburgh, PA (US); Craig Wilcox, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 374 days.

This patent is subject to a terminal disclaimer.

(21) Appl. No.: 10/189,107

(22) Filed: Jul. 1, 2002

(65) Prior Publication Data

US 2003/0027240 A1 Feb. 6, 2003

Related U.S. Application Data

(63) Continuation-in-part of application No. 09/753,592, filed on Jan. 3, 2001, now Pat. No. 6,544,800, which is a continuation of application No. 09/111,610, filed on Jul. 7, 1998, now Pat. No. 6,187,599, which is a continuation of application No. 08/819,240, filed on Mar. 17, 1997, now Pat. No. 5,854,078, which is a continuation-in-part of application No. 08/743,816, filed on Nov. 6, 1996, now Pat. No. 5,898,004.

(60) Provisional application No. 60/302,189, filed on Jun. 29, 2001.

(51) Int. Cl.
| | |
|---|---|
| G01N 33/66 | (2006.01) |
| G01N 21/31 | (2006.01) |
| G01N 21/63 | (2006.01) |
| A61F 2/14 | (2006.01) |

(52) U.S. Cl. .......................... 436/94; 436/95; 436/164; 435/14; 424/422; 424/427; 424/429

(58) Field of Classification Search .................. 436/94, 436/95, 164; 435/14; 424/422, 429, 427
See application file for complete search history.

(56) References Cited

U.S. PATENT DOCUMENTS

| 4,627,689 | A | 12/1986 | Asher | .......................... 359/296 |
|---|---|---|---|---|
| 4,632,517 | A | 12/1986 | Asher | .......................... 359/296 |
| 5,266,238 | A | 11/1993 | Haacke et al. | ............... 252/582 |
| 5,281,370 | A | 1/1994 | Asher et al. | ................. 264/1.1 |
| 5,330,685 | A | 7/1994 | Panzer et al. | ............... 252/582 |
| 5,338,492 | A | 8/1994 | Panzer et al. | ............... 252/582 |
| 5,342,552 | A | 8/1994 | Panzer et al. | ............... 252/582 |
| 5,368,781 | A | 11/1994 | Haacke et al. | ............... 252/582 |
| 5,854,078 | A | 12/1998 | Asher et al. | ................. 436/133 |
| 5,898,004 | A | 4/1999 | Asher et al. | ................. 436/518 |
| 6,187,599 | B1 | 2/2001 | Asher et al. | ................. 436/531 |

OTHER PUBLICATIONS

James and Shinkai, "Artificial Receptors as Chemosensors for Carbohydrates", *Top Curr. Chem.*, 2002, 218:159-200.

Gabai et al., "Characterization of the Swelling of Acrylamidophenylboronic Acid—Acrylamide Hydrogels Upon Interaction with Glucose by Faradaic Impedance Spectroscopy, Chronopotentiometry, Quartz-Crystal Microbalance (QCM), and Surface Plasmon Resonance (SPR) Experiments", *J. Phys. Chem. B.*, 2001, 105:8196-8202.

Arnold et al, "A membrane-moderated, conductimetric sensor for the detection and measurement of specific organic solutes in aqueous solutions", *J. Embr. Sci.*, 2000, 167:227-239.

Jung et al. (2000) "Catalase Effects on Glucose-Sensitive Hydrogels", *Macromolecules*, 33:3332-3336.

Ballerstadt et al. "A fluorescence affinity hollow fiber sensor for continuous transdermal glucose monitoring", Anal. Chem. 2000 Sep. 1;72(17):4185-4192.

Lee et al., "Photonic Crystal Chemical Sensors: pH and Ionic Strength", *J. Am. Chem. Soc. 122*:9534-9537 (2000).

Reese et al., "Synthesis of Highly Charged, Monodisperse Polystyrene Colloidal Particles for the Fabrication of Photonic Crystals", *Journal of Colloid and Interface Science 232*:76-80 (2000).

Yarnitzky et al., "Hand-held lead analyzer", *Talanta*, 51:333-338 (2000).

Podual et al. "Dynamic behavior of glucose oxidase-containing microparticles of poly(ethylene glycol)-grafted cationic hydrogels in an environment of changing pH", Biomaterials Jul. 2000; 21(14):1439-1450.

Rolinski et al., "A time resolved near-infrared fluorescence assay for glucose: opportunities for trans-dermal sensing", *J. Photochem. Photobiol. B: Biology*, 54:26-34 (2000).

Barbour et al., "Experimental Evidence for Alkali-Metal Ion Cation—π Interactions Using Bibracchial Lariat Ether Complexes",*Ind. Eng. Chem. Res.*, 2000, 39:3436-3441.

Yu et al., "Determination of Lead in Blood and Urine by SPME/GC", *Anal. Chem.*, 71:2998-3002 (1999).

Pickup et al., "In vivo glucose sensing for diabetes management: progress towards non-invasive monitoring", *BMJ*, 319:1-4 (1999).

(Continued)

*Primary Examiner*—Mary E. Ceperley
(74) *Attorney, Agent, or Firm*—Arent Fox, PLLC

(57) ABSTRACT

The present invention is related to glucose sensors that are capable of detecting the concentration or level of glucose in a solution or fluid having either low or high ionic strength. The glucose sensors of the present invention comprise a polymerized crystalline colloidal array (PCCA) and a molecular recognition component capable of responding to glucose. The molecular recognition component may be a boronic acid, such as a phenylboronic acid, glucose oxidase, a combination of phenylboronic acid and poly(ethylene) glycol or crown ether, or another component capable of detecting glucose in various fluids and solutions. The glucose sensors of the present invention may be useful in the development of noninvasive or minimally invasive in vivo glucose sensors for patients having diabetes mellitus.

37 Claims, 12 Drawing Sheets

OTHER PUBLICATIONS

Kanekiyo et al., "Molecular-imprinting of AMP utilizing the polyion complex formation process as detected by a QCM system", *J. Chem. Soc. Perkin Trans. 2*, 1999, 2719-2722.

de la Riva et al., "Flow-through room temperature phosphorescence optosensing for the determination of lead in sea water", *Anal. Chim. Acta*, 395:1-9 (1999).

Sawada et al. "Partition and complex formation of alkali metal ion with long chain poly(oxyethylene) derivatives in 1,2-dichloroethane", *Phys. Chem, Chem. Phys.*, 1999, 1:2737-2741.

Gabriely et al. "Transcutaneous glucose measurement using near-infrared spectroscopy during hypoglycemia", Diabetes Care, Dec. 1999;22(12):2026-2032.

MacKenzie et al., "Advances in Photoacoustic Noninvasive Glucose Testing", *Clinical Chemistry*, 45:1587-1595 (1999).

Holtz et al., "Intelligent Polymerized Crystalline Colloidal Arrays: Novel Chemical Sensor Materials", *Anal. Chem.*, 1998, 70:780-791.

Reeder et al., "Electrochemical characterization of microfabricated thick-film carbon sensor for trace determination of lead", *Sensors and Actuators B*, 52:58-64 (1998).

Arnold et al. "Phantom glucose calibration models from simulated noninvasive human near-infrared spectra", Anal Chem May 1, 1998;70(9):1773-1781.

Tamada et al., "In Vivo Studies of a Non-Invasive Glucose Monitor in Subjects with Diabetes", *Diabetes*, 47:Supp. 1, 62A (1998).

English et al., "Polymer and solution ion shielding in polyampholytic hydrogels", *Polymer* 39:5893-5897 (1998).

Davidson MB. "Diabetes research and diabetes care. Where do we stand?", Diabetes Care. Dec. 1998;21(12):2152-2160.

Heinemann et al. "Non-invasive continuous glucose monitoring in Type I diabetic patients with optical glucose sensors. Non-Invasive Task Force (NITF)", Diabetologia Jul. 1998;41(7):848-854.

Marvin et al., "Engineering Biosensors by Introducing Fluorescent Allosteric Signal Transducers: Construction of a Novel Glucose Sensor", *J. Am. Chem. Soc.*, 120:7-11 (1998).

Clark, Jr., CM. "Reducing the burden of diabetes", The National Diabetes Education Program. Diabetes Care. Dec. 1998;21 Suppl 3:C30-1.

Schwarte et al., *Polym. Prepr.*, 38:596 (1997).

Pan et al., "Optically Nonlinear Bragg Diffracting Nanosecond Optical Switches", *Phys. Rev. Lett.* 78:3860-3863 (1997).

Marvin et al. "The rational design of allosteric interactions in a monomeric protein and its applications to the construction of biosensors", Proc Natl Acad Sci USA Apr. 29, 1997;94(9):4366-4371.

Ballerat-Busserolles et al. "Thermodynamics in Micellar Solutions: Confirmation of Complex Formation between Sodium Dodecyl Sulfate and Polyethylene Glycol", *Langmuir*, 1997, 13:1946-1951.

Holtz et al. "Polymerized colloidal crystal hydrogel films as intelligent chemical sensing materials", Nature Oct. 23, 1997;389:829-832.

Liu et al., "Fortuitously Superimposed Lattice Plane Secondary Diffraction from Crystalline Colloidal Arrays", *J. Am. Chem. Soc.* 119:2729-2732 (1997).

Mafé et al., "Multiple Phases in Ionic Copolymer Gels", *Phys. Rev. Lett.* 79:3086-3089 (1997).

English et al., "Equilibrium and non-equilibrium phase in copolymer polyelectrolyte hydrogels", *J. Chem. Phys.* 107:1645-1654 (1997).

James et al. "Fluorescent saccharide receptors: a sweet solution to the design, assembly and evaluation of boronic acid derived PET sensors", *Chem. Commun.*, 1996, 281-288.

Kikuchi, et al., "Glucose-Sensing Electrode Coated with Polymer Complex Gel Containing Phenylboronic Acid", Anal. Chem., vol. 68, pp. 823-828 (1996).

Weissman et al., "Thermally Switchable Periodicities and Diffraction from Mesoscopically Ordered Materials", *Science* 274:959-960 (1996).

Bell et al. "Water, solute and protein diffusion in physiologically responsive hydrogels of poly (methacrylic acid-g-ethylene glycol)", Biomaterials Jun. 1996;17(12):1203-1218.

Dorski et al. "Glucose-Responsive, Complexation Hydrogels", *Polym. Prepr.*, 37:475-476 (1996).

Asher et al. "Optically Nonlinear Crystalline Colloidal Self Assembled Submicron Periodic Structures for Optical Limiters", *Mat. Res. Soc. Symp. Proc. 374*:305-310 (1995).

James et al. "Recognition of sugars and related compounds by "reading-out"-type interfaces", *Supramol. Chem.*, 1995, 6:141-157.

Shibayama et al. "Small-angle neutron scattering study on weakly charged poly(N-isopropyl acrylamide-co-acrylic acid) copolymer solutions", *J. Chem. Phys.* 102:9392-9400 (1995).

James et al. "Chiral discrimination of monosaccharides using a fluorescent molecular sensor", *Nature*, 1995 374:345-347.

Deng et al. "Allosteric Interaction of Metal Ions with Saccharides in a Crowned Diboronic Acid", *J. Am. Chem. Soc.*, 1994, 116:4567-4572.

James et al. "A Glucose-Selective Molecular Fluorescence Sensor", *Angew. Chem., Int. Ed.*, 1994, 33:2207-2209.

Shiomi et al. "Specific Complexation of Glucose with a Diphenylmethane-3,3'-diboronic Acid Derivative: Correlation between the Absolute Configuration of Mono- and Di-saccharides and the Circular Dichroic Activity of the complex", *J. Chem. Soc., Perkin Trans. 1*, 1993, 17:2111-2117.

Okano, T. "Molecular Design of Temperature-Responsive Polymers as Intelligent Materials", *Adv. Polym Sci.* 110:179-197 (1993).

Singhal et al. "Boronate affinity chromatography", Adv. Chromatogr. 1992;31:293-335.

Yoon and Czarnik, "Fluorescent Chemosensors of Carbohydrates. A Means of Chemically Communicating the Binding of Polyols in Water Based on Chelation-Enhanced Quenching", *J. Am. Chem. Soc.* 1992. 114:5874-5875.

Annaka et al. "Multiple phases of polymer gels", *Nature 355*:430-432, (1992).

Boutelle et al. "Enzyme packed bed system for the on-line measurement of glucose, glutamate, and lactate in brain microdialysate", Anal. Chem. Sep. 1, 1992;64(17):1790-1794.

Wilson et al. "Progress toward the development of an implantable sensor for glucose", Clin. Chem. Sep. 1992;38(9)1613-1617.

Asher et al. "New Nonlinear Bragg Diffraction Devices", *SPIE vol. 1626 Nonlinear Optics III*, 238-242 (1992).

Kesavamoorthy et al. "Nanosecond Photothermal Dynamics in Colloidal Suspension", *J. Appl. Phys.* 71:1116-1123 (1992).

Singhal et al. "New ligands for boronate affinity chromatography synthesis and properties", *J. Chromatogr.*, 1991, 543:17-38.

Okada, T. "Characterization of Poly(oxyethylene) Complex Formation with Alkali-metal Cations in a Cation-exchange Resin Phase", J. Chem. Cos. Faraday Trans., 1991, 87:3027-3032.

Kitano et al., "Glucose-responsive complex formation between poly (vinyl alcohol) and poly (N-vinyl-2pyrrolidone) with pendent phenylboronic acid moieties", *Makromol. Chem., Rapid Commun.*, 12, 227-233 (1991).

Trettnak et al. "Fully reversible fibre-optic glucose biosensor based on the intrinsic fluoresence of glucose oxidate", *Analytica Chimica Acta*, 221:195-203 (1989).

Rundquist et al. "Dynamical Bragg Diffraction From Crystalline Colloidal Arrays", *J. Chem. Phys.* 91:4932-4941 (1989).

Soundararajan et al. "Boronic acids for affinity chromatography: spectral methods for determinations of ionization and diol-binding constants", Anal Biochem Apr. 1989;178(1):125-134.

Asher et al. "Crystalline Colloidal Bragg Diffraction Devices: The Basis for a New Generation of Raman Instrumentation", *Spectroscopy* 1:26-31 (1986).

Hirokawa et al. "Volume phase transition in a nonionic gel", *J. Chem. Phys. 81*:6379-6380 (1984).

Sienkiewicz and Roberts, "pH Dependence of Boronic acid-diol affinity in aqueous solution", *J. Inorg. Nucl. Chem.*, 1980, 42:1559-1575.

Weith et al. "Synthesis of cellulose derivatives containing the dihydroxyboryl group and a study of their capacity to form specific complexes with sugars and nucleic acid components", Biochemistry Oct. 27, 1970;9(22):4396-4401.

Inman et al. "The derivatization of cross-linked polyacrylamide beads. Controlled introduction of functional groups for the preparation of special-purpose, biochemical adsorbents", Biochemistry Oct. 1969;8(10):4074-4082.

Vanderhoff et al. "Well-Characterized Monodisperse Latexes", *Journal of Colloid and Interface Science* 28:336-337 (1968).

Lorand and Edwards, "Polyol Complexes and Structure of the Benzeneboronate Ion", *J. Org. Chem.*, 1959, 24:769-774.

Kesavamoorthy et al., "Thermally Switchcable Laser Diffracting Gels", *Laser Applications in Material Science and Industry*, 265-273 (1997).

Asher et al., "Crystalline Colloidal Array Optical Switching Devices", *Nanoparticles in Solids and Solutions*, NATO ASI Series vol. 18, pp. 65-69 (1996).

INTELLIGENT POLYMERIZED CRYSTALLINE COLLOIDAL ARRAY CARBOHYDRATE SENSORS

CROSS-REFERENCE TO RELATED APPLICATIONS

This application is a continuation-in-part of U.S. patent application Ser. No. 09/753,592, filed Jan. 3, 2001 now U.S. Pat. No. 6,544,800, which is a continuation of U.S. patent application Ser. No. 09/111,610, filed Jul. 7, 1998, now U.S. Pat. No. 6,187,599, which is a continuation of U.S. patent application Ser. No. 08/819,240, filed Mar. 17, 1997, now U.S. Pat. No. 5,854,078, which is a continuation-in-part of U.S. patent application Ser. No. 08/743,816, filed Nov. 6, 1996, now U.S. Pat. No. 5,898,004. This application also claims priority to U.S. Provisional Patent Application Ser. No. 60/302,189, filed Jun. 29, 2001.

This invention was made with government support under Contract No. 1-R01 DK55348-01 awarded by the National Institute of Health. Therefore, the government has certain rights in the invention.

FIELD OF THE INVENTION

The present invention generally relates to polymerized crystalline colloidal array (PCCA) chemical sensing materials that are able to detect the concentration or level of a carbohydrate, such as glucose, in both low and high ionic strength solutions. The PCCA sensing materials comprise a molecular recognition component that is capable of binding with the carbohydrate of interest. In a particularly preferred embodiment of the invention, a glucose sensor is disclosed that comprises a boronic acid, such as 3-fluoro-4-aminophenylboronic acid, as the molecular recognition component in the PCCA chemical sensing materials. The present invention further relates to a method for determining the concentration of a carbohydrate, such as glucose, in a fluid or solution, such as blood, tear fluid, interstitial fluid or other bodily fluids and glucose solutions, and in fermentation through the use of a hydrogel PCCA chemical sensing material that has been functionalized with a molecular recognition component capable of binding to the carbohydrate of interest.

BACKGROUND OF THE INVENTION

An ever-increasing demand exists for materials and methods that provide continuous, noninvasive or minimally invasive glucose monitoring because of the increase in the number of people diagnosed with diabetes mellitus, more commonly referred to as type 1, insulin dependent diabetes. Clark, Jr., *Diabetes Care*, 21:Supp. 3, C1 (1998); Davidson, *Diabetes Care*, 21:2152 (1999). The need for minimally invasive glucose monitoring has also increased due to the recognition that the long-term health of patients with diabetes mellitus is dramatically improved with careful glucose monitoring and control. Picup et al., *BMJ*, 319:1289 (1999). However, many methodologies for glucose monitoring are invasive and often show poor patient compliance, which leads to negative health consequences for the patient.

The need for minimally invasive, easy-to-use glucose sensors and methods of detecting glucose concentration has motivated the investigation of numerous approaches. For example, early work in near-infrared absorption spectroscopy, which took advantage of tissue transparency in the 600 to 1300 nm spectral range, showed initial promise as a truly non-invasive glucose sensor. Heinemann et al., *Diabetologia*, 41:848 (1998). In this technique, near-infrared radiation is allowed to penetrate biological tissues within the therapeutic window of 600 to 1300 nm, and the spectrum of the tissue is then acquired through either a transmission or a reflectance measurement. Arnold et al., *Anal. Chem.*, 70:1773 (1998). The acquired spectrum contains a mixture of overlapping spectral bands for the various components of the tissue, such as water, fat, protein, and glucose, and the spectrum is used to determine the level of glucose in the tissue. However, the accuracy of this technique is negatively affected by factors such as blood flow and temperature, which are difficult to control.

Various optical methods have also been investigated for noninvasive glucose monitoring. For example, luminescent glucose sensors have been developed based on the intrinsic green fluorescence of the glucose oxidase enzyme (referred to herein as "GOD"), the enzyme involved in the conversion of glucose to gluconic acid. Trettnak et al., *Analytica Chimica Acta*, 221:195 (1989). The flavin moiety, which is present at the active site of the GOD, becomes reduced when glucose is converted to gluconic acid. Because the flavin moiety and its reduced form exhibit different fluorescence spectra, the change in the fluorescence spectrum of the GOD may be monitored to determine the glucose concentration in a solution or fluid.

Other researchers have attached fluorescent probes to the GOD molecule for fluorescence-based glucose sensing, since the binding of glucose to the GOD molecule changes the fluorescence probe. James et al., *Angewandte Chemie Int'l Edition in English*, 33:2207 (1994). In another approach, fluorescent probes are attached to glucose binding proteins (also called maltose binding proteins), where the glucose binding proteins undergo dramatic conformational changes which alter the fluorescence of the probe. Marvin et al., *Proc. Natl. Acad. Sci., USA*, 94:4366 (1997); Marvin et al., *J. Am. Chem. Soc.*, 120:7 (1998). Additionally, other techniques such as photoacoustic spectroscopy (MacKenzie et al., *Clinical Chemistry*, 45:1487 (1999)), near-infrared absorption spectroscopy (Gabriely, et al., *Diabetes Care*, 22:2026 (2000)), and near-infrared fluorescence spectroscopy (Rolinski et al., *J. Photochem. Photobiol. B: Biology*, 54:26 (2000)) have also been investigated for determining the level of glucose in tissues.

Recently, various minimally invasive approaches to glucose monitoring have attempted to determine glucose levels in extracted interstitial fluid. These approaches utilize microdialysis (Boutelle et al., Anal. Chem., 64:1790 (1992)) or electric fields (Tamada et al., *Diabetes*, 47:Supp. 1, 62A (1998)) to obtain the interstitial fluids through the skin, and such techniques use primarily electrochemical methods to determine the glucose concentration. The last approach has been commercialized as a watch-type device to electrochemically determine the glucose level in fluid that is extracted through the skin. Picup et al., *BMJ* 319:1289 (1999). However, the perspiration on a patient's skin may interfere with the accuracy of such a watch-type device.

More invasive approaches of glucose monitoring involve the implantation of electrochemical and fluorescent sensors in tissue. For example, one approach provides for the monitoring of the intensity of the fluorescence of the glucose sensors through the skin by using small external spectrometers. Ballerstadt et al., *Anal. Chem.*, 72:4185 (2000). Other approaches provide for the implantation of electrochemical glucose sensors within the body, and some of these approaches utilize external circuits to determine the electrochemical signals given off by the glucose sensors, while others completely implant the sensors and utilize various remote readouts to monitor glucose levels. Wilson et al., *Clin. Chem.*, 1613 (1992). All of these approaches to glucose monitoring face the challenges of sensor stability, tissue rejection, ease of use, and cost.

A variety of electrochemical glucose sensors are known in the art. One such electrochemical glucose sensor involves an amperometric enzyme electrode, which uses immobilized glucose oxidase (GOD). Generally, the conversion of glucose to gluconic acid can be described by the following reaction scheme:

$$\text{GOD-FAD} + \beta\text{-D-glucose} \rightarrow \text{GOD-FAD·H}_2 + \text{D-glucono-}\delta\text{-lactone}$$

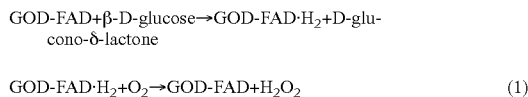  (1)

wherein "FAD" represents the flavine-adenine dinucleotide prosthetic group that is attached to the GOD enzyme, while FAD·H$_2$ represents the reduced form of FAD. Referring to the above reaction scheme, GOD amperometric sensors are able to monitor the concentration of glucose by monitoring the change in the flow of current caused by the electrochemical reduction of hydrogen peroxide as shown in the reaction designated "(1)" in the above scheme.

Another electrochemical glucose sensor that utilizes GOD involves the use of pH-responsive hydrogels. Dorski et al., *Polym. Prepr.*, 37:475 (1996); Podual et al., *Biomaterials*, 21:1439 (2000); Jung et al., *Macromolecules*, 33:3332 (2000). The GOD-induced catalysis of glucose to gluconic acid results in a decrease in the pH of the solution. This pH decrease actuates the swelling or shrinking of the hydrogel materials. These hydrogel volume changes alter the diffusion constant of electrochemically active species in the solution. The resultant changes in the electrochemistry (for example, changes in conductivity and current flow) may be used to monitor the glucose concentration. Such an approach may also be useful for developing in vivo insulin supplying devices. Schwarte et al., Polym. Prepr., 38:596 (1997); Bell et al., *Biomaterials*, 17:2023 (1996). This type of electrochemical approach to detecting glucose in a solution require the use of electrical wires and instrumentation.

Other electrochemical approaches for monitoring glucose levels in fluids have utilized polymer hydrogels that have been functionalized with phenylboronic acids, which bind glucose and other diols. Kitano et al., *Makromol. Chem., Rapid Commun.*, 12, 227–233 (1991). The binding of glucose results in the swelling or shrinking of a hydrogel, where the hydrogel is coated on the surface of an electrode. The changing volume of the hydrogel is monitored through its effects on the diffusion constant of electrochemically active species with respect to the electrode. Even though the detection scheme for measuring glucose levels disclosed by Kitano et al. employs a hydrogel that swells and shrinks, such an electrochemical sensing method requires the use of electrical wires and instrumentation in order to detect glucose levels. Thus, a hydrogel glucose sensor according to Kitano et al. could not be used in a contact lens type format nor as an optical insert, as it would be impossible to connect electrical wires and/or instrumentation to the sensor while the sensor is in a patient's eye.

As mentioned above, some glucose sensors known in the art have employed polymer hydrogels. For example, glucose sensing materials have been disclosed which comprise a polyacrylamide hydrogel wherein a crystalline colloidal array is embedded. The polymerized crystalline colloidal array chemical sensing materials (which have been referred to as "PCCA"s) have been described in, for example, U.S. Pat. Nos. 6,187,599, 5,854,078, and 5,898,004, all of which are hereby incorporated by reference in their entireties herein. Such PCCA materials have been described with respect to their ability to detect metal cations, pH, ionic strength, and the concentration or level of glucose.

In previous disclosures where PCCA chemical sensing materials have been used in conjunction with measuring levels of glucose, the sensing materials have relied upon GOD, the enzyme described earlier. Specifically, the conversion of glucose to gluconic acid, which is catalyzed by the GOD enzyme, results in the reduction of FAD, whereby the FAD becomes negatively charged and causes the hydrogel (in which the PCCA is embedded) to swell. This swelling of the hydrogel results in a red-shift of the Bragg diffraction, which enables a user to determine the concentration of glucose.

A need exists for the development of accurate, reliable, continuous, and noninvasive or minimally invasive glucose sensors that may improve the lives of patients having diabetes and may decrease such patients' risk of developing hypoglycemia and hyperglycemia.

SUMMARY OF THE INVENTION

The present invention is directed to a glucose sensing material that is useful for continuous monitoring of the glucose levels in both low and high ionic strength solutions. The glucose sensor material of the present invention comprises a polymerized crystalline colloidal array (PCCA), which is embedded in a polyacrylamide hydrogel, wherein the PCCA has been functionalized with a molecular recognition component capable of measuring glucose levels, either directly or indirectly.

The PCCA glucose sensors described herein may be used as part of a contact lens that a patient would use to detect the glucose level in tear fluid. Similarly, the PCCA glucose sensors of the present invention may be used as part of an optical insert, which would be placed under the lower eyelid of a patient in order to determine glucose levels in that patient's tear fluid. Likewise, the PCCA glucose sensors of this invention may be implanted under the skin of a patient in order to measure the glucose concentration in the interstitial fluid of a patient. These and other uses for the PCCA glucose sensors of the present invention reveal that these sensors are useful in glucose detection schemes that are minimally invasive or noninvasive when compared to known glucose detection schemes (such as electrochemical methods and the like) that are more invasive to a patient.

As earlier stated, the PCCA glucose sensors of the present invention comprise a molecular recognition component that is capable of detecting glucose. Thus, the molecular recognition component must be a component that is capable of binding to glucose, where glucose contains cis-diols. Suitable molecular recognition components that bind with diols include, but are not limited to dihydroxides of boron, barium, calcium, magnesium, and strontium. In preferred embodiments of the present invention, dihydroxides of boron and strontium are used as the molecular recognition component. Dihydroxides of boron, having the formula R—B(OH)$_2$ may be preferred, where R is at least one arene group.

Specific boronic acid derivatives that may be used as the molecular recognition component in the glucose sensors of the present invention include, but are not limited to: phenylboronic acid; p-nitrophenylboronic acid, 4-methoxyphenylboronic acid, α-naphthylboronic acid, 4-aminomethyl-2-

N,N'-dimethylaminomethylphenylboronic acid, 3-fluoro-4-aminophenylboronic acid, and other arene boronic acids and their derivatives.

Additionally, the molecular recognition component in the PCCA glucose sensor may be glucose oxidase (GOD), a combination of phenylboronic acid and poly(ethylene)glycol (PEG), or a combination of phenylboronic acid with a crown ether. The type of molecular recognition component to be used in the PCCA glucose sensors of the present invention may be determined by the salinity level or the ionic strength of the solution to be measured. For example, if a patient's tear fluid is the solution in which the level of glucose is to be measured, the molecular recognition component to be used in the glucose sensor would be one that effectively binds to glucose at the physiological salinity level of human tear fluid and actuates a hydrogel volume change. Thus, in certain preferred embodiments, the level of glucose in a high ionic strength solution may be measured with a PCCA glucose sensor where the molecular recognition component in the sensor is a boronic acid derivative, such as 3-fluoro-4-aminophenylboronic acid, combined with PEG or where the molecular recognition component is a boronic acid derivative, such as 3-fluoro-4-aminophenylboronic acid, combined with a crown ether.

The glucose sensor materials of the present invention are able to detect the concentration of glucose found in fluids such as blood, interstitial fluid, tear fluid, and the like, and the glucose sensor materials are able to detect glucose levels in solutions or fluids having physiological salinity levels. Furthermore, the PCCA glucose sensors are useful for both subcutaneous and extraocular glucose sensing. For example, the PCCA glucose sensor may make up a small, unobtrusive part of a contact lens for a patient, and the patient would be able to use a mirror in order to observe the lens color, which would then be compared to a color chart in order to determine the glucose concentration in the patient's tear fluid. The glucose level in tear fluid has been shown to track the glucose level in blood. In applications where the glucose sensors are used as subcutaneous implants, the PCCA glucose sensor is implanted under the skin of a patient, and the patient can continuously monitor the blood glucose concentration by observing the diffracted color visually or with a spectrometer or a spectrophotometer.

The glucose sensors of the present invention work by diffracting light from the polymerized crystalline colloidal array, wherein dramatic color changes can be observed over ranges of glucose concentration that are physiologically typical. Specifically, the PCCA glucose sensor comprises a cubic array of colloidal particles polymerized in a hydrogel. The PCCA diffracts light of a wavelength determined by the array spacing. Exposure to glucose alters the hydrogel volume, which changes the array spacing and thereby alters the diffracted wavelength.

The glucose sensor materials of the present invention are minimally invasive or noninvasive for use in patients having diabetes. The sensor materials disclosed herein exhibit selectivity for glucose when compared to other sugars that are of physiological importance.

In certain preferred embodiments of the invention where the glucose concentration in a low ionic strength solution is to be determined, 3-aminophenylboronic acid is used as the molecular recognition component in the PCCA glucose sensor.

The present invention is further described below with respect to certain specific embodiments.

BRIEF DESCRIPTION OF THE DRAWINGS

Further objects and advantages of the present invention will be more fully appreciated from a reading of the detailed description when considered with the accompanying drawings, wherein.

DETAILED DESCRIPTION OF THE INVENTION

Figure 1:
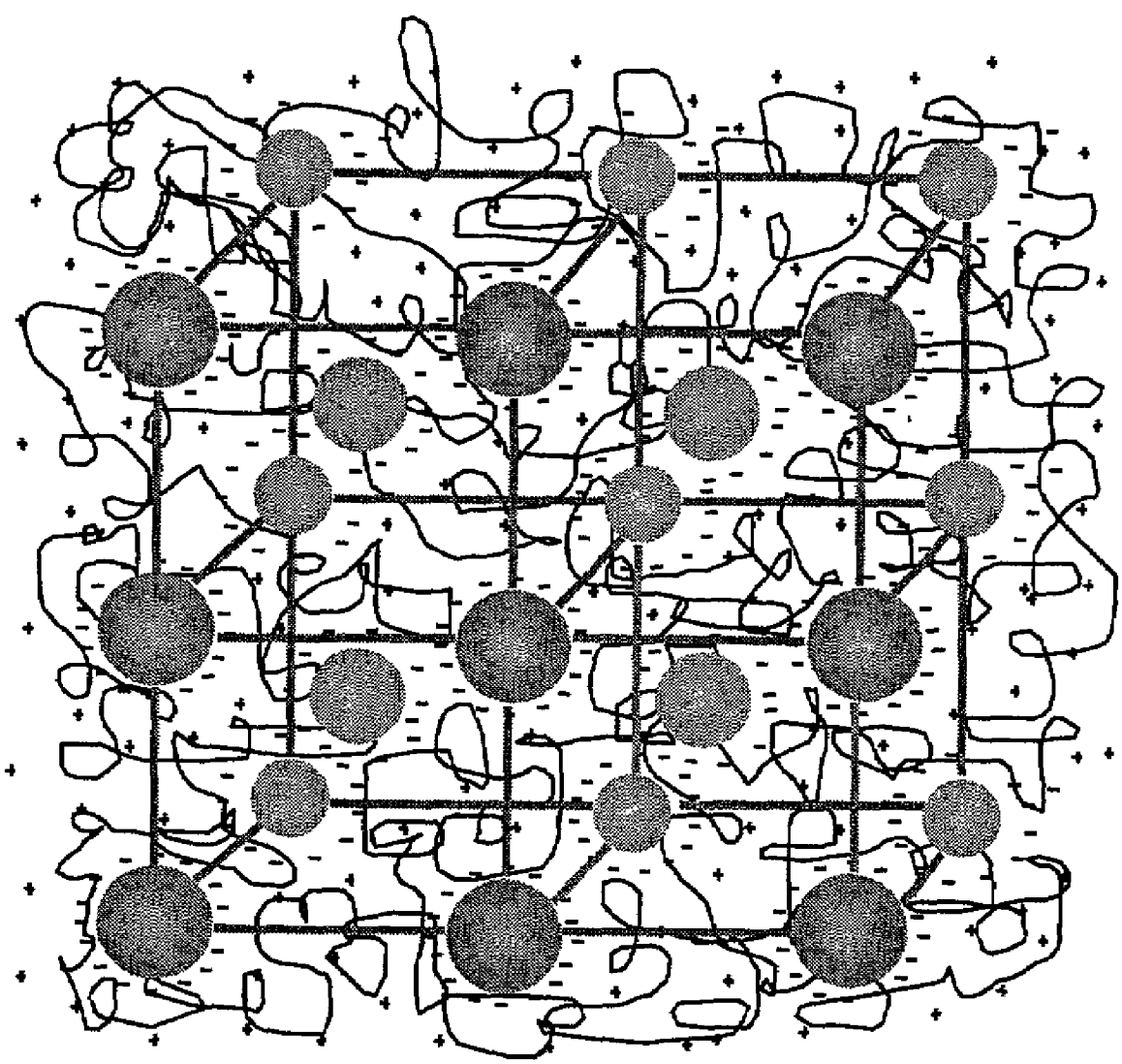
FIG. 1 shows a polymerized crystalline colloidal array (PCCA) sensor material consisting of a polymer hydrogel network with an embedded CCA which contains a molecular recognition component.

The present invention is directed to glucose sensors which are capable of detecting the level or concentration of glucose in a solution or a fluid, where that solution or fluid may have either a high ionic strength or a low ionic strength. Specifically, the glucose sensors disclosed herein comprise a crystalline colloidal array (CCA) that is polymerized in a hydrogel, where the hydrogel undergoes a volume change in response to the presence of glucose. Such CCAs polymerized in a hydrogel have been disclosed in U.S. Pat. Nos. 6,187,599, 5,898,004 and 5,854,078, incorporated herein by reference.

The glucose sensor devices of the present invention generally comprise a hydrogel, where the hydrogel undergoes a volume change in response to the presence of glucose, and a light diffracting crystalline colloidal array of charged particles polymerized in the hydrogel. The crystalline colloidal array has a lattice spacing that changes when the volume of the hydrogel changes, thereby causing the light diffraction of the crystalline colloidal array to change. Thus, these devices are optical, gel-based glucose sensors that combine the light diffraction properties of crystalline colloidal arrays (CCAs) with the confoirmational changes that various polymers undergo in response to external stimuli.

The hydrogel in one embodiment of the present invention generally comprises a crosslinking agent, a gel component and a molecular recognition component. The crosslinking agent can be any crosslinking agent compatible with the other components of the hydrogel. Examples of suitable crosslinkers include, but are not limited to, N,N'-methylenebisacrylamide, methylenebismethacrylamide and ethyleneglycol-dimethacrylate, with N,N'-methylenebisacrylamide being preferred. In addition to forming the polymer network in the CCA, the cross-linking agent described herein assists in the formation of the hydrogel and strengthens the resulting hydrogel film so that a self-supporting film results.

The glucose sensor of the present invention comprises a molecular recognition component capable of detecting glucose. In certain embodiments, glucose oxidase (GOD) is the molecular recognition component. In other preferred embodiments, phenylboronic acid, or more specifically, 3-amino-4-flurophenylboronic acid, is the molecular recognition component. In still other preferred embodiments, the polymerized crystalline colloidal array (PCCA) has been functionalized with both phenylboronic acid and poly(ethylene)glycol (PEG). Likewise, in certain preferred embodiments, the PCCA has been functionalized with phenylboronic acid and a crown ether.

Specifically, the volume phase transition properties of the PCCA hydrogel are modified by functionalizing the hydrogel with a molecular recognition component that specifically binds to glucose, the species of interest to be detected in the present invention. Thus, the PCCA hydrogel is modified so as to detect the presence of glucose through a molecular recognition process where the molecular recognition component interacts with glucose. Generally, the more of the molecular recognition component that is incorporated into the PCCA hydrogel, the more sensitive the sensor device is to glucose. This relationship, however, is only observed up to a certain concentration of the molecular recognition component, after which the sensitivity of the PCCA hydrogel may decrease.

It is contemplated that the glucose sensors disclosed herein are useful in vivo for patients having diabetes mellitus. The method of using the PCCA glucose sensors of the present invention is a minimally invasive detection scheme when compared to those glucose detection schemes generally known in the art.

In one embodiment of the present invention, a glucose sensor is disclosed which comprises a PCCA embedded within a polyacrylamide hydrogel. The polyacrylamide hydrogel PCCA has pendent boronic acid groups attached thereto as a result of being functionalized by phenylboronic acid. Thus, phenylboronic acid acts as the molecular recognition component in these embodiments. Such a glucose sensor is able to detect glucose levels in solutions having low ionic strengths. Herein, solutions having low ionic strengths typically include those solutions with a salt concentration of about 0–10 mM (while solutions having a salt concentration of greater than about 10 mM are considered to be high ionic strength solutions).

When the glucose sensor of the present embodiment is used in a low ionic strength solution or fluid containing glucose, the diffraction from the sensor red shifts as the concentration of glucose increases. This red shifting is due to the swelling of the hydrogel network. Specifically, the swelling of the hydrogel network results from water flowing into the hydrogel matrix. This water flow is induced by an osmotic pressure, which is generated by the ionization of the glucose-linked boronic acid functional groups that have been attached to the polyacrylamide hydrogel PCCA. The ionization of the boronic acid groups is the result of a decrease in the $pK_a$ of the boronic acid which is caused by the binding of the boronic acid groups to glucose.

In another embodiment of the present invention, a glucose sensor is disclosed which comprises a PCCA embedded within a polyacrylamide hydrogel, where the PCCA hydrogel has been functionalized by phenylboronic acid and either poly(ethylene)glycol (PEG) or crown ether. The glucose sensor of this embodiment is able to detect levels of glucose in solutions having high ionic strengths (ionic strengths that are physiologically typical). A glucose sensor according to this embodiment exhibits a diffraction blue shift (rather than the red shift described above for the glucose sensor not containing PEG or crown ether) as the glucose concentration increases from a concentration of about 0.1 mM to about 10 mM. However, at very high glucose concentrations, which are not physiologically typical for tear fluid, the glucose sensor of this embodiment exhibits a red shift in diffraction. If the sensor of this embodiment is being used to measure the glucose concentration in tear fluid, for example, then only the blue shift in diffraction will be observed for increasing glucose concentration.

In embodiments where a boronic acid, such as 3-fluoro-4-aminophenylboronic acid, acts as a molecular recognition component for the glucose sensor, the functionalization of the PCCA to add the boronic acid groups to the PCCA may take place via two different routes: a hydrazine routed a hydrolysis route, both of which are described in more detail below.

In still other embodiments of the present invention, a glucose sensor is disclosed which comprises a CCA embedded within a polyacrylamide hydrogel, where the PCCA hydrogel has been functionalized by glucose oxidase (GOD) as the molecular recognition component.

In certain embodiments of the present invention, a molecular recognition component other than GOD, phenylboronic acid, or phenylboronic acid combined with either PEG or crown ether may be used, so long as the molecular recognition component is capable of interacting with glucose and actuating a hydrogel volume change. The skilled artisan would appreciate how to determine glucose levels when other such molecular recognition components are employed. For example, they can utilize a molecular recognition component that can change hydrogel pH, which can change the hydrogel free energy of mixing.

An important function of the sensors and the detection methods disclosed by the present invention is the ability to effectively detect glucose at concentrations that are physiologically typical in human bodily fluids and the like. For example, the concentration of glucose in human tear fluid is generally known to be from about 0.1 mM to about 0.4 mM. Altman et al. eds., *Biology Data Book, Second Edition*, Vol. III, pg. 2039. Also, a higher concentration of up to about 1.2 mM of glucose may be expected in the tear fluid of children of ages 6–38 months. The disclosure of the present invention shows that the glucose sensing materials described herein are able to detect such glucose concentrations in human and artificial tear fluid. Additionally, the glucose concentration in human blood has been reported to be about 0.3 mM to about 50 mM. The glucose sensors described herein and the glucose detection method are effective at such glucose concentrations in human blood.

Generally, the volume phase transitions of the PCCA hydrogel material used in the glucose sensors of the present invention are driven by the balance between the free energy of mixing of the hydrogel with the medium ($\Delta G_{mix}$), the ionic interactions, such as the formation of a Donnan potential ($\Delta G_{ion}$) and the free energy associated with the elastic restoring force which results from hydrogel crosslinking ($\Delta G_{elas}$). Thus for the equation:

$$\Delta G = \Delta G_{mix} + \Delta G_{elas} + \Delta G_{ion}$$

the equilibrium hydrogel volume is determined when $\Delta G=0$.

The ionic interaction portion of the free energy ($\Delta G_{ion}$) is negligible at high ionic strengths. Thus, the hydrogel volume is determined by the balance between the free energy of mixing and the elastic restoring force. The free energy of mixing should not change dramatically with the addition of low concentrations of sugars. Thus, the major term giving rise to hydrogel volume phase transitions is the elastic restoring force. The major factor determining the elastic free energy is the amount of crosslinking in the hydrogel. Thus, not wishing to be bound by theory, it is contemplated that the sensor mechanism is intimately related to phenomena that cause variations in hydrogel crosslinking.

The present invention may be better understood through the working Examples detailed below. These Examples are intended to illustrate the invention and should not be construed as limiting the invention in any way.

EXAMPLES

Example 1

Preparation of Crystalline Colloidal Arrays (CCAs)

Highly charged, monodisperse polystyrene colloids were prepared by emulsion polymerization as described in Reese et al., *J. Colloid Interface Sci.*, 232:76–80 (2000), which is hereby incorporated by reference in its entirety. Specifically, suspensions comprising about 5–10 weight % of ~140 nm polystyrene colloidal particles were used. The suspensions were cleaned by dialysis using deionized water (specifically using the Barnstead Nanopure Water Purification System at 17.5 MΩ-cm) and by shaking with ion-exchange resin. The suspension became iridescent due to Bragg diffraction from the CCA upon shaking with ion-exchange resin. Specifically, each particle possesses ~60,000–70,000 strong acid groups.

Example 2

Preparation of Acrylamide Polymerized Crystalline Colloidal Arrays (PCCAs)

In this Example, acrylamide polymerized crystalline colloidal arrays (PCCAs) were synthesized by a free radical solution polymerization process which utilized diethoxyacetophenone (DEAP) as a photoinitiator. Specifically, about 100 mg (1.4 mmol) of acrylamide, 5 mg (33.7 µmol) of bis-acrylamide, and 2 g of the CCA suspension (in an amount of about 8–10 weight %) were combined in deionized water along with 50 mg of ion-exchange resin. This polymerization mixture was shaken for about 10–15 minutes and was deoxygenated by nitrogen bubbling. About 7.7 µL of a 10% solution of DEAP in DMSO (3.84 µmol of DEAP) was added to the acrylamide-bisacrylamide-CCA (bisCCA) suspension, and the solution was shaken for an additional 10 minutes. Subsequently, the solution was centrifuged for 30 seconds in order to precipitate the resin particles. The resulting dispersion was injected into a cell consisting of two clean quartz discs separated by either a 125 µm Parafilm film or by two 40 µm Duraseal spacers. Generally, the PCCA of this Example was prepared according to the disclosures of U.S. Pat. Nos. 6,187,599, 5,898,004, and 5,854,078, incorporated herein by reference.

Photopolymerization was performed under UV mercury lamps at a wavelength of 365 nm for about 40–60 minutes. The cells were then opened and the PCCAs were washed overnight in about 10 liters of distilled water. The dimensions of the PCCAs formed were about 25 mm×25 mm. FIG. 1 is a depiction of a PCCA that may be used in the glucose sensors of the present invention.

Example 3

Chemical Modification of PCCA to Incorporate Phenylboronic Acid Molecular Recognition Component to Form Glucose Sensor The Examples above focused on the formation of the polymerized crystalline colloidal arrays (PCCAs) embedded in acrylamide hydrogel. Once a PCCA has been formed, it is necessary to chemically modify the hydrogel backbone of the PCCA in order to functionalize the PCCA with a molecular recognition component that is capable of binding glucose. Specifically, when a boronic acid such as 3-aminophenylboronic acid is used, two routes are available for this chemical modification of the PCCAs, and these routes are shown in Scheme 1 below:

Scheme 1 (Two Routes to Chemically Modify the PCCA Hydrogel Backbone)

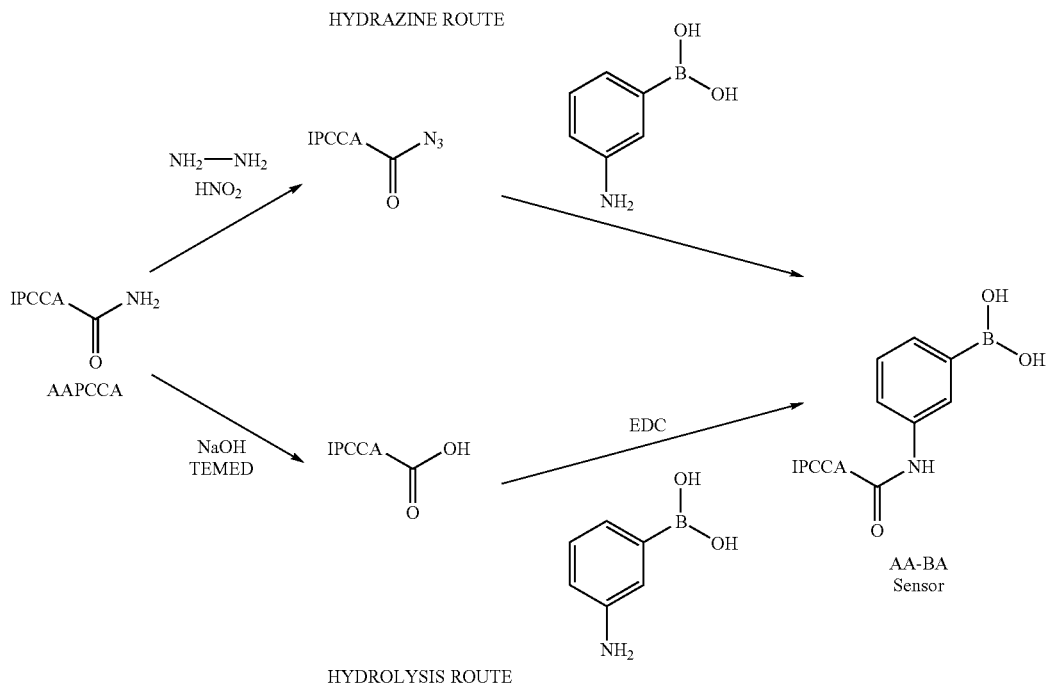

In embodiments where the "hydrazine route" shown above was utilized for chemically modifying the PCCA material, acylazide groups were attached to the PCCA hydrogel backbone in order to link them to the 3-aminophenylboronic acid. The hydrazine treatment was performed as described by Inman et al., *Biochemistry*, 1969, 8, 4074; and Weith et al., *Biochemistry*, 1970, 9, 4396, both of which are hereby incorporated by reference in their entireties. First, 25 mL of 6 M aqueous hydrazine solution was preheated to 47° C. for about 45 minutes. Then, the PCCA hydrogel was immersed in this warm hydrazine solution at 47° C. for 1 hour. This resulted in a PCCA hydrogel containing acyl hydrazine side chains.

After repeated washings with 0.1 M NaCl aqueous solutions and with cooled distilled water, the gel was immersed in a nitrous acid solution (32 mL of 0.25 M HCl in 10 mL of 1 M $NaNO_2$) in an ice bath for 20 minutes. The resulting acylazine gel was then repeatedly washed with a 0.1 M NaCl solution and cold distilled water. Subsequently, the boronic acid function groups were attached to the acylazide-functionalized PCCA by immersing the PCCA in a solution of 3-aminophenylboronic acid having a concentration of about 0.1–0.2 M and having a pH of about 8.5. This addition of the boronic acid groups took place in an ice bath for 1–2 days.

The amount of boronic acid attached to the PCCA was determined from the decrease in the 280 nm UV absorption of the boronic acid coupling solution, after correcting the absorption for the boronic acid extracted after two washings. Typically, about 0.5 mmol of boronic acid was incorporated per gram of the PCCA. Thus, about 9% of the —$CONH_2$ groups in the original PCCA were substituted by boronic acid moieties. This functionalizing procedure should also convert some (less than 2%) of the amide groups to carboxylic groups. The remaining azide groups were removed by treating the PCCA with 0.1 M $NH_4OH$ for about 20 minutes.

The second route depicted in Scheme 1 above to obtain a PCCA glucose sensor that has been functionalized with boronic acid groups involves hydrolysis of the PCCA amide groups. Specifically, the PCCA was placed in a 0.1 N NaOH solution containing 10% v/v tetramethylethylenediamine (TEMED) for 1.5–2 hours. The hydrolyzed PCCA was then washed repeatedly with distilled water and was immersed in a solution containing 20 mM 1-[3-(dimethylamino)propyl]-3-ethylcarbodiimide hydrochloride (EDC) and 20 mM 3-aminophenylboronic acid for about 2–4 hours, to obtain the boronic acid-functionalized-PCCA glucose sensor (denoted as a "BA-PCCA" for short). The resulting BA-PCCA glucose sensors were repeatedly washed with distilled water.

Because of carboxyl ionization, the washed hydrolyzed gels extensively swell in water and diffract in the IR region. The diffraction of the PCCA after boronic acid attachment returned almost to that of the original non-hydrolyzed PCCA, indicating that most of the carboxyl groups formed amide bonds with the boronic acid groups. Typically, about 1 mmol boronic acid was incorporated per gram of PCCA.

Example 4

Glucose Detection in Low Ionic Strength Solutions Using BA-PCCA Glucose Sensor

Boronic acid has a high $pK_a$ and is primarily neutral at a pH of 8.5. The binding of glucose decreases the $pK_a$ of boronic acid. Thus, at pH 8.5 a proton is released to form the glucose-boronate anion conjugate base as shown in Scheme 2 below:

Scheme 2

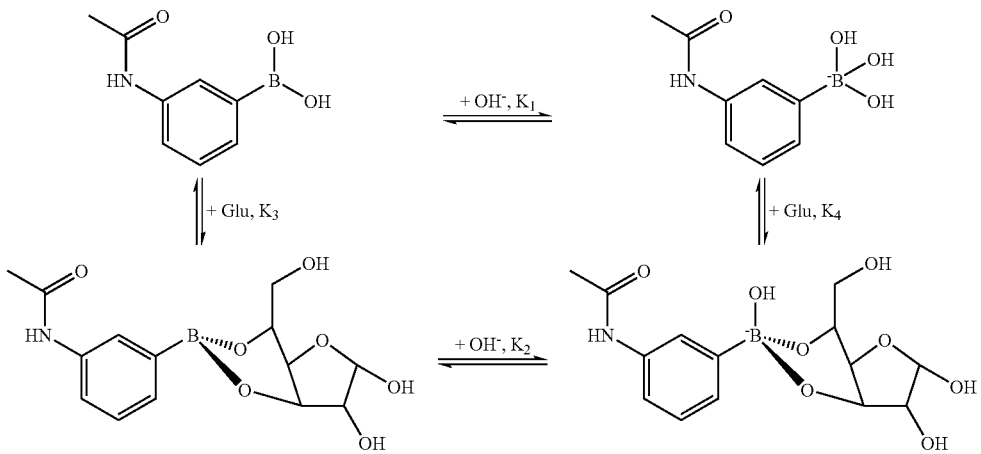

Specifically, Scheme 2 shows the acid-base equilibrium that occurs when carbohydrate is bound to phenylboronic acid.

Figure 2:
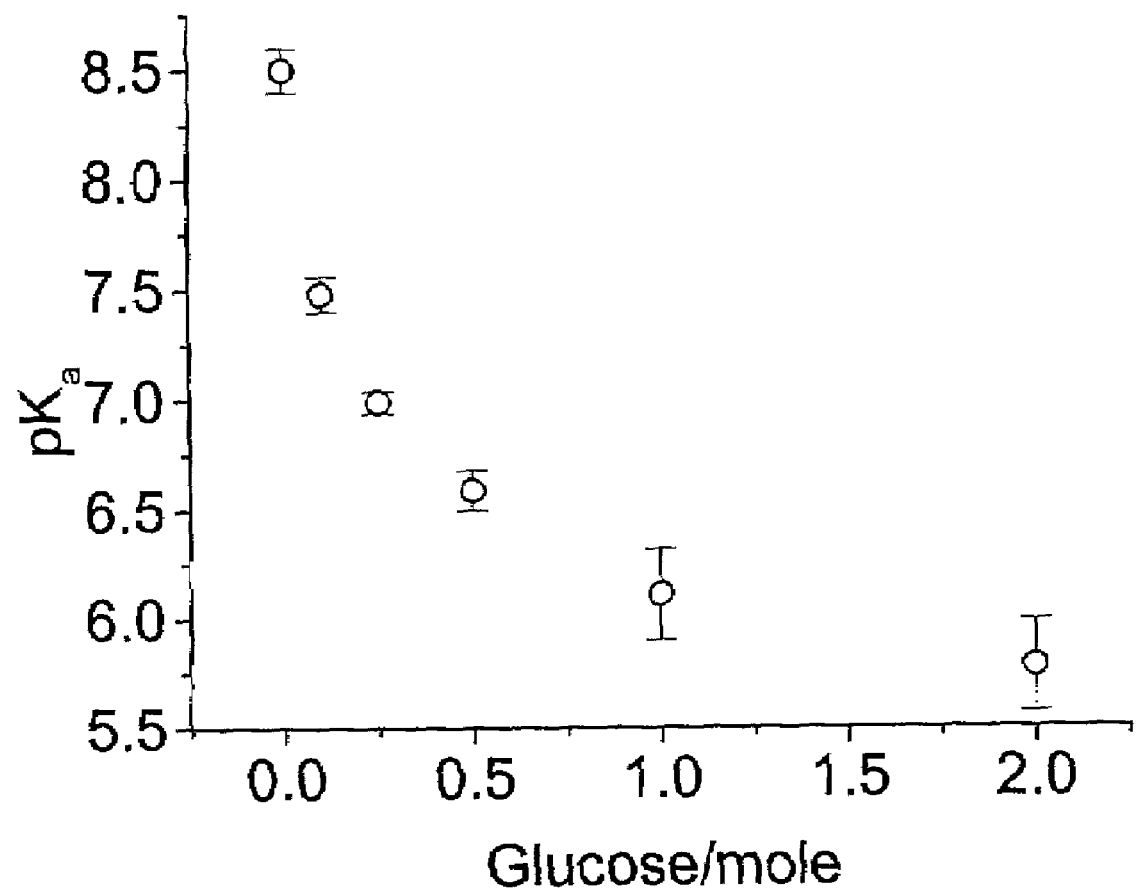
FIG. 2 shows a plot of the dependence of pKa shift of a 0.05 mM (3-acetamidophenyl)boronic acid aqueous solution on glucose concentration.

It is well documented that the $pK_a$ of boronic acid drops upon glucose binding. See, e.g., James and Shinkai, *Top Curr. Chem.*, 2002, 218:159–200; James, Sandanayake, and Shinkai, *Supramol. Chem.*, 1995, 6:141–157; Arnold, Zheng, and Michaels, *J. Embr. Sci.*, 2000, 167:227–239; Singhal, and Desilva, *Adv. Chromatogr.*, 1992, 31:293–336; Singhal et al., *J. Chromatogr.*, 1991, 27:1061–1062; Lorand and Edwards, *J. Org. Chem.*, 1959, 24:769–774; Sienkiewicz and Roberts, *J. Inorg. Nucl. Chem.*, 1980, 42:1559–1575; and Soundararajan et al., *Anal Biochem.*, 1989, 178:125–134. FIG. 2 shows the $pK_a$ values for (3-acetomidophenyl)boronic acid in the presence of different concentrations of glucose determined by titration in aqueous solution and monitored by using UV absorption spectroscopy.

The $pK_a$ shift of boronic acid upon sugar binding was first utilized by James et al. (*Chem. Commun.*, 1996, 281–288) and by Yoon and Czarnik (*J. Am. Chem. Soc.*, 1992, 114: 5874–5875) who coupled the $pK_a$ shift to fluorescence changes for sugar sensing. See James, Sandanayake and Shinkai, *Angew. Chem., Int. Ed.*, 1994, 33:2207–2209 and James, Sandanayake and Shinkai, *Nature*, 1995374:345–347. The mechanism also operates in boronic acid hydrogel materials. See, e.g., Kanekiyo et al., *J. Chem. Soc. Perkin Trans.* 2, 1999, 2719–2722; Gabai et al., *J. Phys. Chem. B.*, 2001, 105:8196–8202; and Arnold, Zheng and Michaels, *J. Membr. Sci.*, 2000, 167:227–239. Arnold et al. demonstrated that for a fixed pH of 8.5, the glucose boronate anion concentration increased approximately linearly with added glucose, until the neutral boronic acid species were exhausted.

Figure 3A:
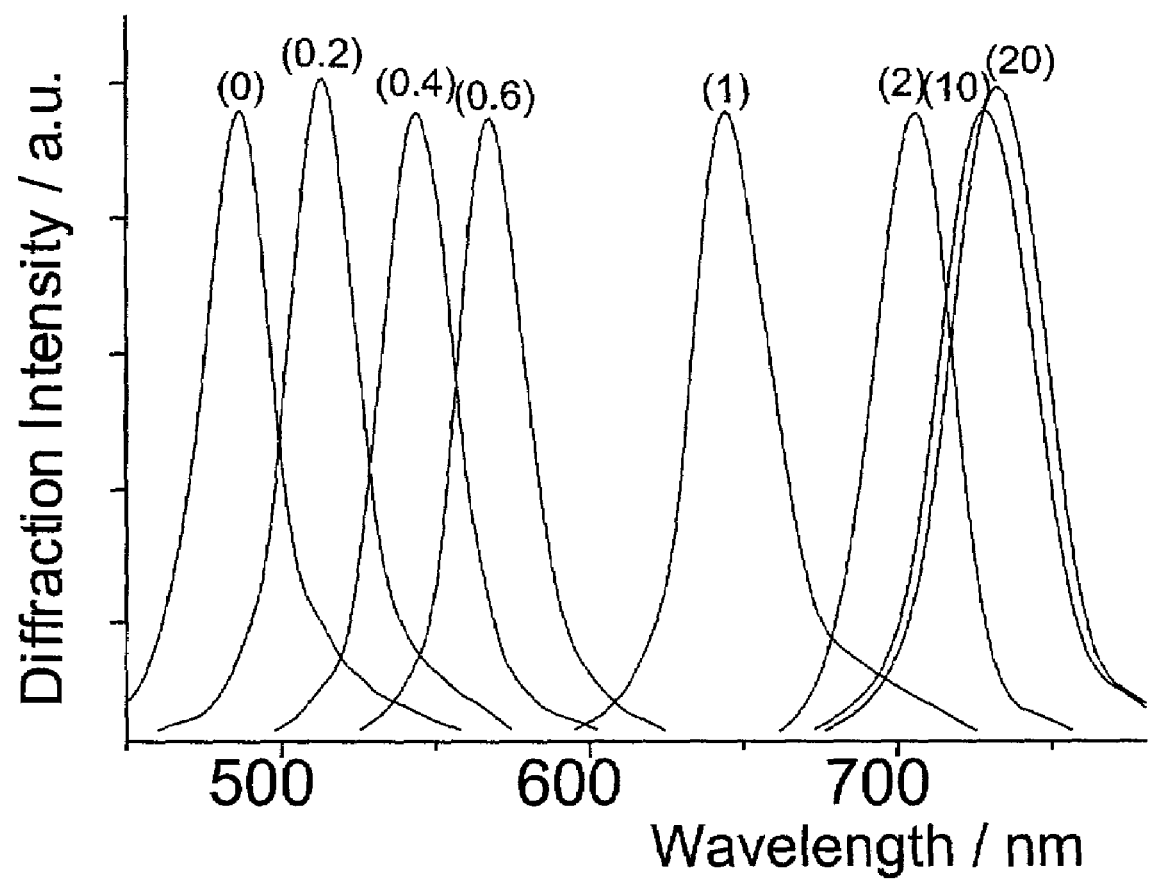
FIG. 3(A) shows the glucose concentration dependence of the diffraction intensity of a boronic acid functionalized PCCA glucose sensor according to an exemplary embodiment of the present invention, where the pH is about 8.5 and where the glucose concentrations are as follows: 0 mM, 0.2 mM, 0.4 mM, 0.6 mM, 1 mM, 2 mM, 10 mM, and 20 mM.
Figure 3B:
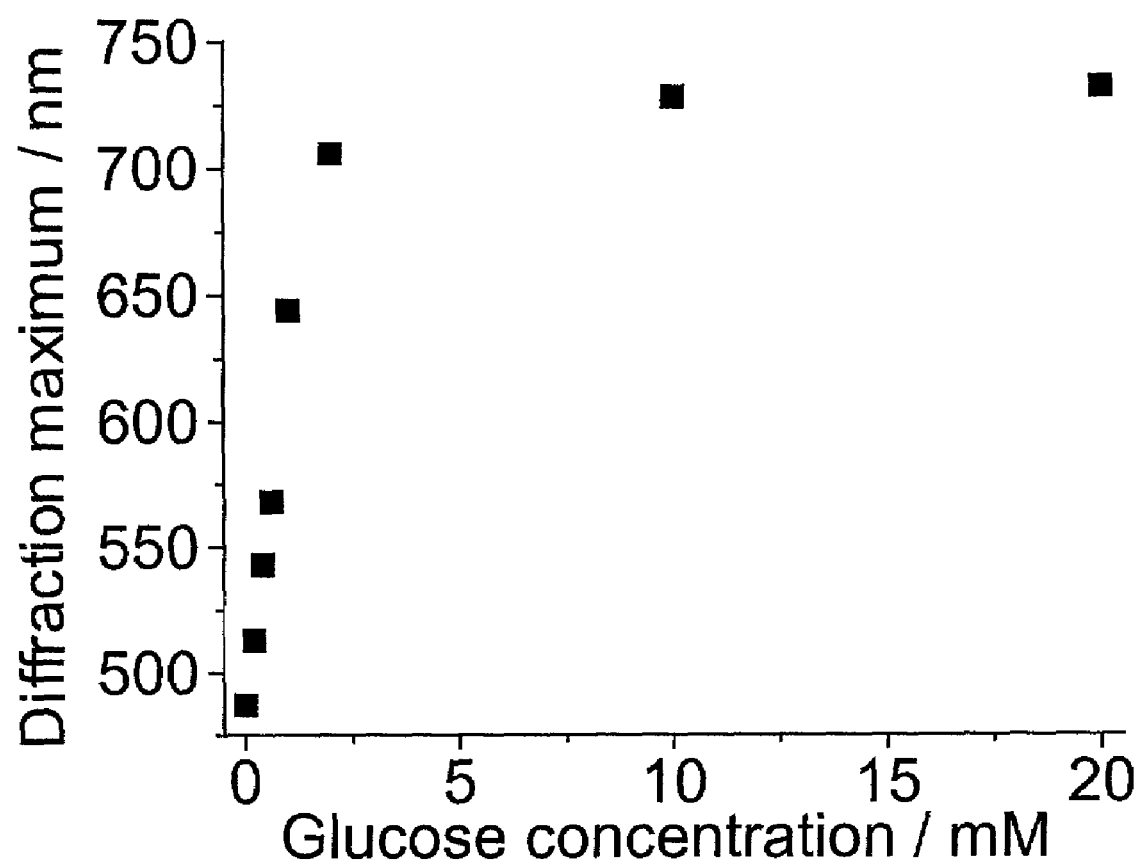
FIG. 3(B) shows a plot of the glucose concentration dependence of the diffraction maximum wavelength of a boronic acid functionalized PCCA glucose sensor according to an exemplary embodiment of the present invention.
Figure 4:
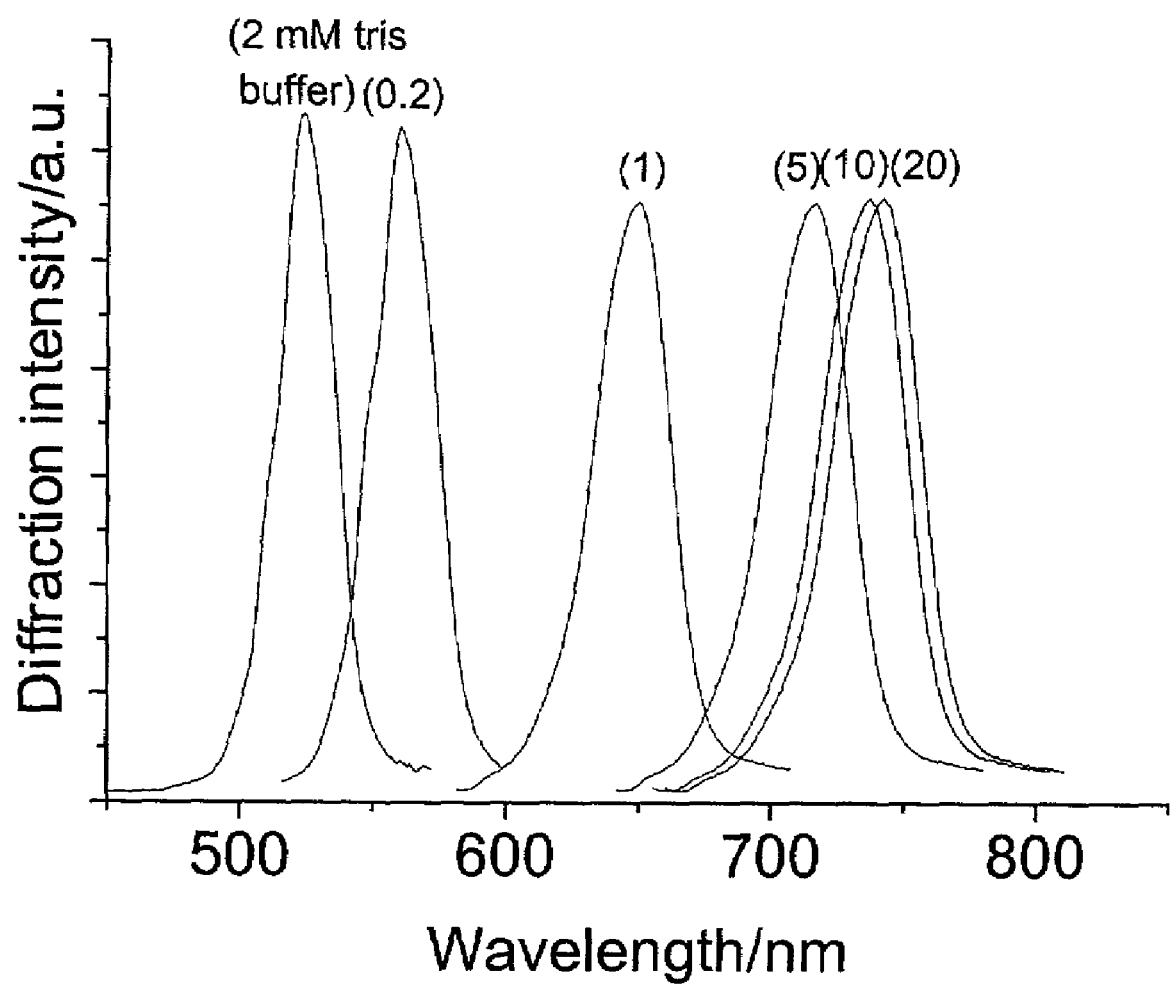
FIG. 4 shows the glucose concentration dependence of the diffraction intensity of a PCCA glucose sensor according to an exemplary embodiment of the invention where the molecular recognition component is (3-acetamidophenyl)boronic acid, where the sensor is studied in a 2 mM buffer solution of tris-hydrochloride, wherein the pH is about 9.5, and where the glucose concentrations are 0 mM, 0.2 mM, 1 mM, 5 mM, 10 mM, and 20 mM.
Figure 5:
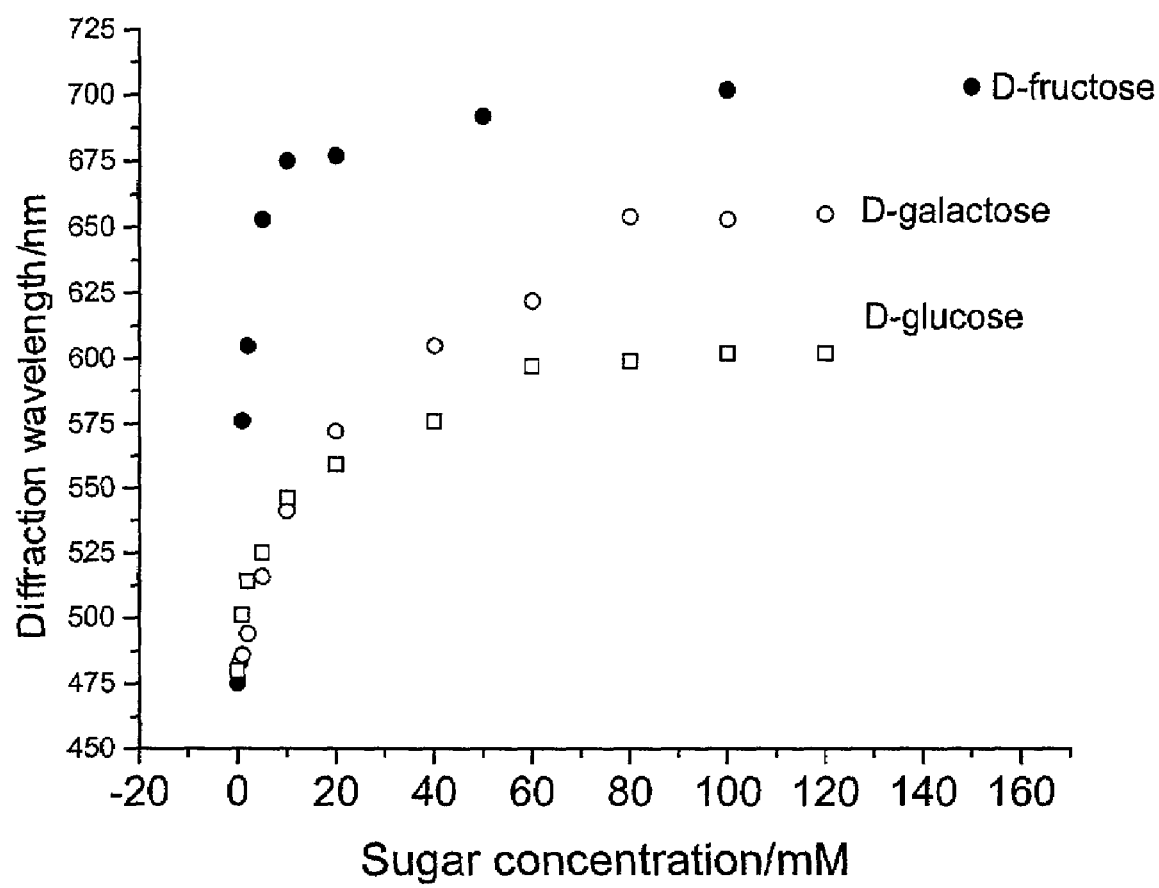
FIG. 5 shows a plot of the diffraction red shifts for a boronic acid functionalized PCCA glucose sensor according to an exemplary embodiment of the present invention, where the sensor has been placed in solutions of three different sugars (D-fructose, D-galactose, and D-glucose) in a 2 mM tris-hydrochloride buffer solution having a pH of about 8.5.

These results allow for the quantitative understanding of the mechanism of operation of the BA-PCCA sensor of the present invention, as described herein. FIG. 3(A) shows the glucose concentration dependence of diffraction of the BA-PCCA sensor of the present invention in water at pH 8.5. The diffraction peak derives from diffraction of normally incident light by the fcc 111 plane of the embedded CCA. See Holtz and Asher, *Nature*, 1997, 389:829–832. Because glucose binding drops the pH, small amounts of NaOH were added to maintain the solution at pH 8.5. In the absence of glucose, the sensor shows a symmetric diffraction peak at 492 nm, indicating that it diffracts blue light. This diffraction peak red shifts as the glucose concentration increases. For example as shown in FIG. 3(A), the sensor diffracts green light at 508 nm with 0.2 mM glucose, orange light at 570 nm with 0.6 mM glucose, and red light at 645 nm with 1 mM glucose. These diffraction red shifts originate from the hydrogel swelling due to the formation of the anionic boronate groups upon glucose binding (see Scheme 2 above). FIG. 3(B) shows that the response is almost linear until it sharply saturates at glucose concentrations above 2 mM, which is consistent with the previous results. See, e.g., Arnold, Sheng and Michaels, *J. Membr. Sci.*, 2000, 167: 227–239. FIG. 4 shows that similar results occur in the presence of 2 mM tris-HCl, pH 8.5 buffer. This response is fully reversible at pH 8.5, such that decreasing glucose concentrations blue shifts the diffraction. The sensing material is not selective toward glucose. As shown in FIG. 5, it binds other clinically relevant sugars such as galactose and fructose. The magnitude of the red shift upon sugar binding is in line with the order of association constants of the various sugars with benzeneboronic acid. i.e. D-fructose>D-galactose>D-glucose. However, the concentrations of sugars such as fructose and galactose are sufficiently low that they will negligibly interfere with the determination of glucose concentration.

The glucose titration diffraction curve shown in FIG. 3(B) results from the drop in boronic acid $pK_a$ induced by glucose binding. The glucose binding is favored by hydroxylation of boronic acid groups. Upon hydroxylation, the boronic acid becomes more negatively charged; glucose binding immobilizes charges on the polymer hydrogel network. This immobilization creates a Donnan potential (Holtz and Asher, *Nature*, 1997, 389:829–832; Lee and Asher, *J. Am. Chem. Soc.*, 2000, 122:9534–9537; and Holtz et al., *Ana. Chem.*, 1998, 70:780–791) which gives rise to an osmotic pressure which swells the hydrogel at low ionic strength and causes the embedded CCA diffraction to red shift.

The BA-PCCA glucose sensors of the present embodiment typically do not respond to glucose in solutions having high ionic strengths, such as in solutions having an ionic strength of greater than about 10 mM NaCl. This is because high ionic strengths decrease the osmotic swelling pressure induced by the Donnan potential mechanism. This may limit the utility of the BA-PCCA glucose sensors of the present embodiment for detecting glucose levels in bodily fluids, which tend to have ionic strengths or salinities of about 150 mM NaCl. However, these BA-PCCA glucose sensors are useful for monitoring glucose levels in low ionic strength solutions, including but not limited to glucose solutions found in the food industry or in ion-exchanged bodily fluids from which salts have been reduced.

Example 5

Preparation of Poly(ethylene)glycol Acrylamide PCCAs (PEG-PCCAs)

PEG-PCCAs were prepared by adding 400 or 200 D molecular weight poly(ethylene glycol) monomethacrylate as a comonomer to the polymerization mixture. The PEG was cleaned by exposing it to ion-exchange resin to remove ionic impurities. Typically, about 80 mg of acrylamide and 20 mg of PEG are combined with the amounts of the colloid, crosslinker and photoinitiator described in Examples 1 and 2 above. Chemical modification of the hydrogel backbone was accomplished as described above. The modification of the hydrogel backbone gave rise to reactive azides or carboxylic groups which were used to attach aminophenyl boronic acid to the acrylamide-PEG network.

Example 6

Glucose Detection Using PEG-BA-PCCA Glucose Sensor

Figure 6A:
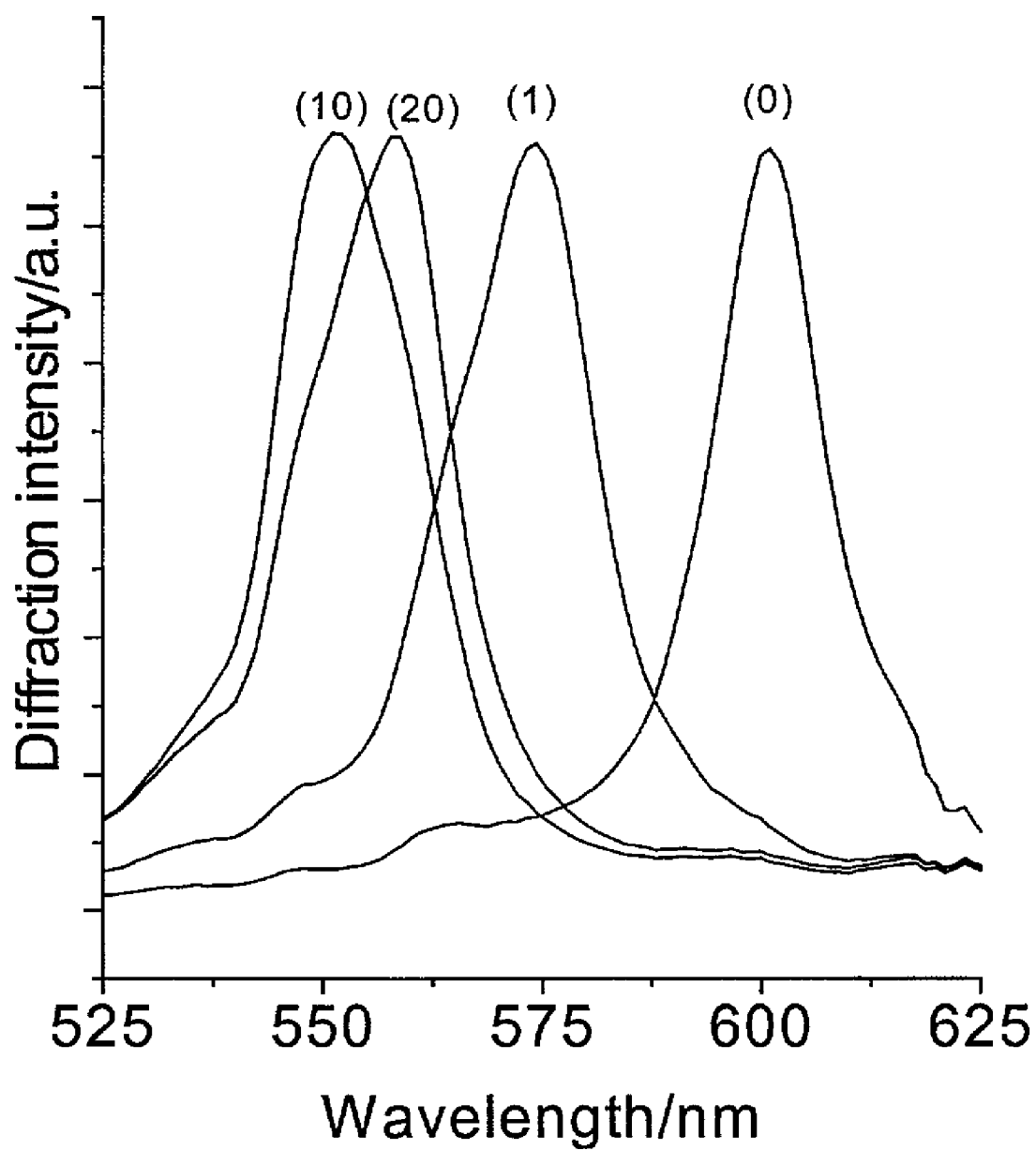
FIG. 6(A) shows the glucose concentration dependence of the diffraction intensity of a PEG-BA-PCCA sensor according to an exemplary embodiment of the present invention in an aqueous solution containing 2 mM tris-hydrochloride buffer and 150 mM NaCl and having a pH of about 8.5, where the glucose concentrations included 0 mM, 1 mM, 10 mM and 20 mM.
Figure 6B:
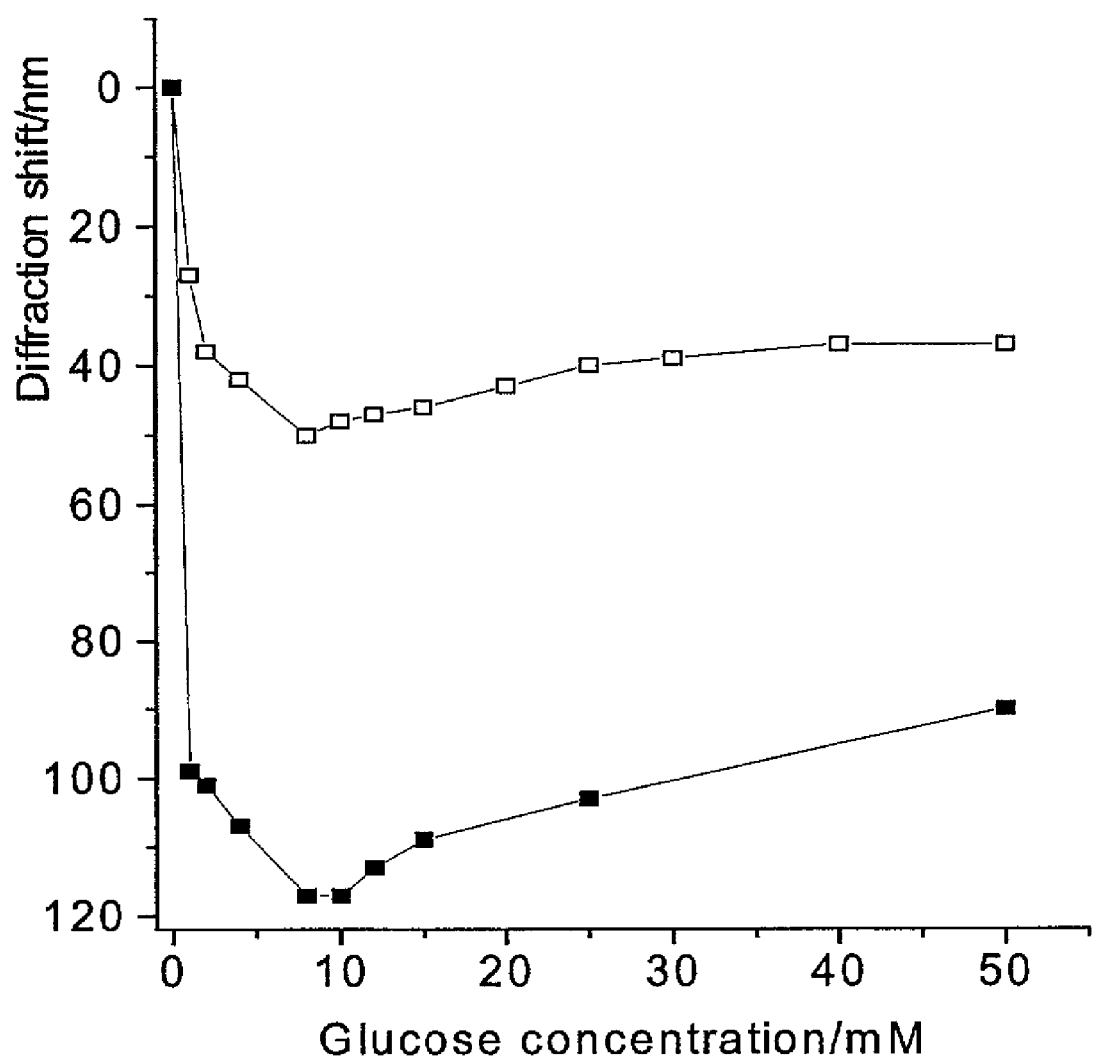
FIG. 6(B) shows the dependence of the diffraction shift on glucose concentration for a PEG-BA-PCCA glucose sensor according to an exemplary embodiment of the invention in a first solution having a pH of about 8.5, containing 2 mM tris-hydrochloride buffer and 150 mM NaCl (represented by the open squares), and a second solution having a pH of about 9.5, containing 100 mM sodium carbonate-bicarbonate buffer and 150 mM NaCl (represented by the filled squares)

FIG. 6 shows the glucose concentration dependence of the diffraction of a PEG-BA-PCCA sensor according to the present invention in a solution having a pH of about 8.5, containing 2 mM tris-HCl buffer and 150 mM NaCl. The spectral peaks result from diffraction by the 111 plane of the embedded face centered cubic CCA. In the absence of glucose, the sensor diffracts 600 nm red light. The diffraction blue shifts for increasing glucose concentrations up to 10 mM glucose, as shown in FIG. 6(B). For example, the PEG-BA-PCCA diffracts 575 and 550 nm light at 1 mM and 10 mM glucose, respectively. Further increases in glucose concentration red shift the diffraction, e.g. at 20 mM glucose, the diffraction occurs at 558 nm. FIG. 6(A) compares the response to glucose at pH 8.5 to the response at pH 9.5. The magnitude of the shift is larger at pH 8.5 due to the increased population of the boronate form which has a higher glucose affinity. This is different than the observations seen above for the BA-PCCA in the absence of PEG which responds to glucose (at the same pH values) because of the decrease in the boronic acid pKa induced by glucose binding due to the creation of boronate ions along the hydrogel polymer network which results in a Donnan potential that induces hydrogel swelling. This phenomenon does not occur at high ionic strength.

Therefore, the response of the PEG-BA-PCCA must result either from changes in the hydrogel elasticity or from changes in the free energy of mixing of the hydrogel with the mainly aqueous environment. See, Flory, *Principles of Polymer Science*, Cornell University Press, Ithaca, N.Y., 1953. Because of the high ionic strength, the response cannot derive from changes in numbers of bound charged species.

Not wanting to be bound by any particular theory, for the PEG-BA-PCCA sensor, the low glucose concentration diffraction blue shift signals a shrinking of the hydrogel with may result from an increase in the hydrogel elastic constant. This elastic constant increase may result from an increase in the hydrogel cross-link density which may result from the formation of glucose cross-links across two boronic acids in the hydrogel. A similar mechanism was shown for D-glucose and D-allose cross-linking to two boronic acids by Shinnka et al. for a bisbornic acid crown ether complex (Deng, James, and Shinkai, *J. Am. Chem. Soc.*, 1994, 116:4567) or for diphenylmethane-3,3'-diboronic acid (Shiomi et al. *J. Chem. Soc., Perkin Trans.* 1, 1993, 17:2111). A less likely, but possible mechanism for the hydrogel shrinkage at low glucose concentrations is a decreased free energy of mixing of the hydrogel upon glucose binding.

Example 7

Determining Glucose Selectivity of PEG-BA-PCCA Glucose Sensors

In order to better understand the mechanism of response for the PEG-BA-PCCA of the present invention, the monosaccharides whose structures are shown in Scheme 3 were examined.

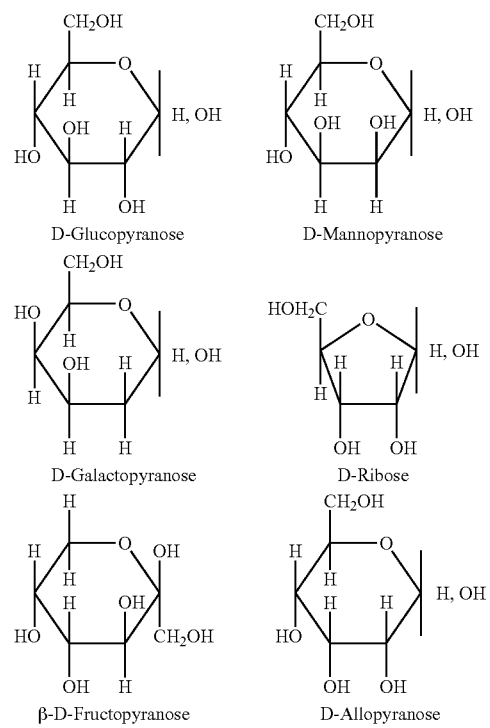

Scheme 3

The response of the PEG-BA-PCCA sensor to these sugars indicates that glucose, allose and ribose form cross-links to shrink the hydrogel, while other sugars bind to single boronates and increase the net free energy of mixing of the hydrogel.

D-allose and D-ribose are unique in the sugars studied since their configuration at the 1,2 positions is identical to glucose, as is the 4,6 diol configuration of D-allose, and as is the 3,5 configuration for D-ribose. Therefore, it is likely that these are the sites of binding of these sugars to boronic acid.

The red shift observed at higher glucose concentrations is likely a result of saturation of the boronate binding sites, where the equilibrium is shifted toward 1:1 BA-glucose complex. This is supported by the observation that addition of free BA to a pH 8.5 solution containing 5 mM glucose and 150 mM NaCl causes the PEG-BA-PCCA sensor to red shift 10 nm. (Data not shown.) While not wishing to be bound by any theory, it is believed that this red shift results from competition of the free BA for the second glucose cis-diol site.

While there is only a very weak glucose response for the BA-PCCA sensor described above in 150 mM NaCl solution at pH 8.5, covalently attached PEG or even PEG added to the buffered salt solution (collectively referred to as PEG-BA-PCCA) in which the glucose is measured, results in a large blue shift upon glucose binding to the PEG-BA-PCCA. For the BA-PCCA sensor, addition of 5 mM and 10 mM glucose in the presence of 2 mM tris and 150 mM NaCl at pH 8.5 results in a small 12 nm blue shift. In comparison, addition of PEG 400 (10% by volume) to the solution results in a 10-fold larger blue shift at 5 mM glucose which further decreases 39 nm for 10 mM glucose. Thus, glucose crosslinking appears to be enhanced by the added PEG. In the absence of 150 mM NaCl, addition of PEG to BA-PCCA results in a large red shift due to the formation of the boronate anion. Addition of PEG results in a 3-fold smaller red shift.

The PEG-BA-PCCA red shifts upon addition of 1 mM salt, whereas there is no response for the BA-PCCA. The red shifts for the PEG-BA-PCCA at 1 mM salt must derive from complexation of cations by the PEG that serves to localize charge on the hydrogel. $Na^+$ appears to be most strongly bound while TMA is least strongly bound. Previous studies have shown that PEG can chelate cations (Barbour et al., *Ind. Eng. Chem. Res.*, 2000, 39:3436; Ballerat-Busserolles, Roux-Desgranges, and Roux, *Langmuir*, 1997, 13:1946; Sawada, Satoh, and Kikuchi, *Phys. Chem, Chem. Phys.*, 1999, 1:2737; Okada, *J. Chem. Cos. Faraday Trans.*, 1991, 87:3027 and *Poly(Ethylene Glycol)Chemistry*, Ed. Harris, Plenum Press, NY 1992), and that short-chain PEGs can form lariate complexes with sodium. Although these observations were made in organic phases where these complexes were exploited as "phase transfer agents", it is likely that they could also exist in aqueous solution.

Figure 7:
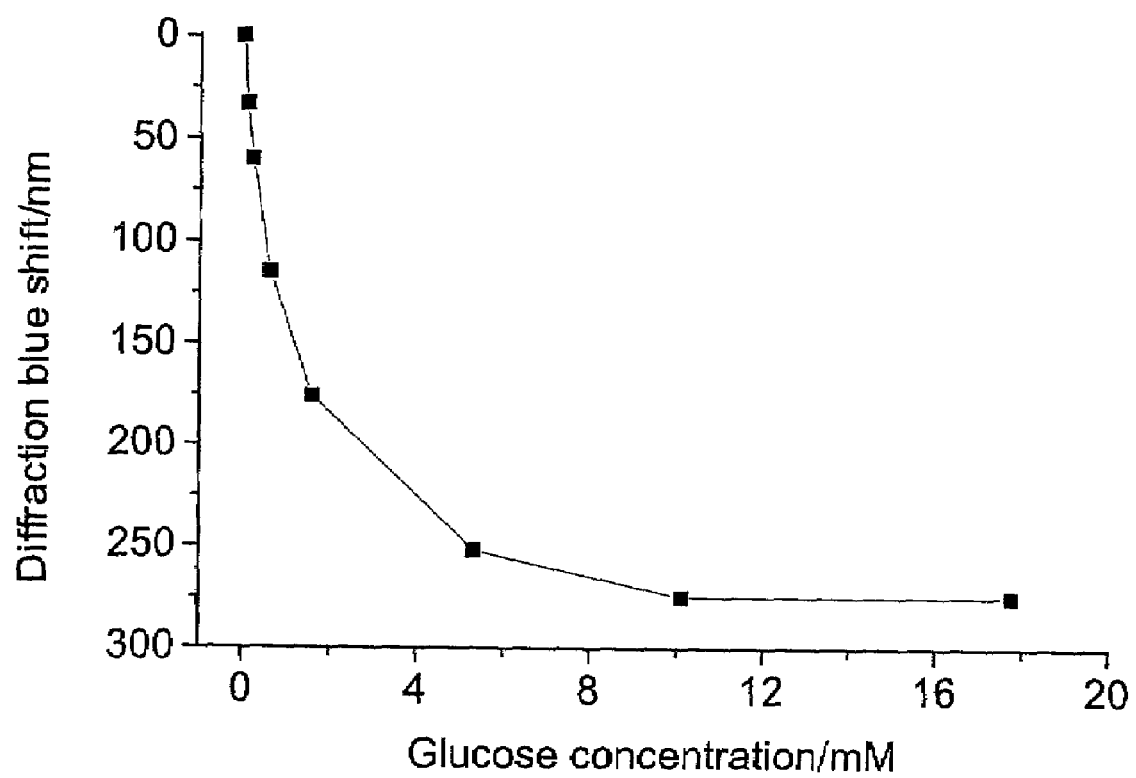
FIG. 7 shows the diffraction blue shift of a BA-PCCA glucose sensor upon the concentration of glucose, where the molecular recognition component comprises a boronic acid as well as 15 crown-5, and where the solution contained 2 mM tris-hydrochloride buffer, 150 mM NaCl and had a pH of about 8.5.

FIG. 7 shows that there is a glucose induced hydrogel shrinking BA-PCCA containing a 15 crown-5 (Acros Organics) instead of PEG. As with PEG, this is likely due to the fact that crown ether has a large association constant for sodium.

The fact that both PEG (or the crown ether) and cations are required for the glucose induced cross-linking blue shift suggests the following mechanism (Scheme 4) for the glucose response of the PEG-BA-PCCA of the invention:

Scheme 4

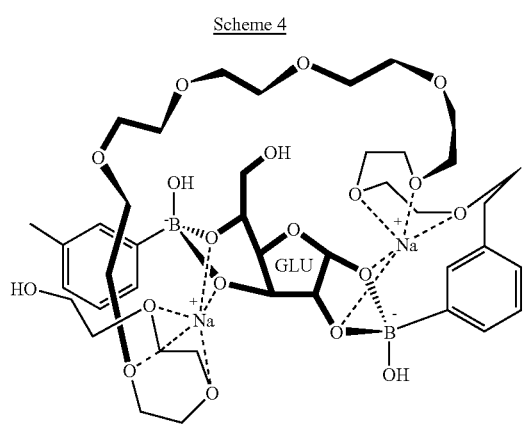

Scheme 4 represents a hypothesized supramolecular complex formed between glucose, two boronates, PEG and sodium cations. According to the hypothesis, the crosslinking glucose is shown in the furanose form, but it could also be in the pyranose form. At low glucose concentrations, the glucose crosslinks two PCCA boronates, while the PEG or crown ether moieties localize cations close to the two boronates to form ion pairs to electrostatically stabilize the di-anion complex by minimizing the electrostatic repulsion between the two anionic boronates. The PEG localizes the cations to dramatically increase their effective concentration. The glucose-induced hydrogel crosslinks increase the elastic restoring force and shrink the hydrogel volume, which blue shifts the diffraction. Higher glucose concentrations saturate the boronate sites to break the glucose crosslinks to red shift the diffraction. Crosslinking with the boronate anion is clear since no response to glucose appears at pH values below 7.5 where the high affinity boronate-glucose anion complex does not form. Data not shown. PEG or crown ethers increase the local cation concentrations to stabilize the glucose bisboronate anion supramolecular complex.

While the PEG-BA-PCCA sensors of the present invention are useful for measuring glucose levels in high ionic strength solutions, they are not optimal for measuring glucose at physiological pH, nor are the BA-PCCA sensors of the present invention.

The response of the glucose sensors of the present invention can be broadened and shifted by changing the sensor composition. For example, by changing the concentration of the crosslinker used in forming the sensor, the sensitivity of the sensor is altered. Also, by using different molecular recognition components, the operational pH range and the operational range of glucose concentrations at which the sensor is effective are altered. By appropriately choosing the molecular recognition component to be used and the amount of that component to include in the sensor, the glucose sensors of the present invention can be optimized for glucose detection in bodily fluids, such as blood, interstitial fluid, and tear fluid. This allows adjustment of the sensor sensitivity for physiologic and pathophysiologic conditions and allows the sensor to be useful in a broad range of applications.

Example 8

Glucose Detection in Artificial Tear Fluid Using BA-PCCA Sensor

As noted above, the BA-PCCA and PEG-BA-PCCA sensors are not optimal for measuring glucose concentrations at physiological pH. Because it is desired to use the sensors of the present invention under physiological conditions, including physiological pH and physiological salt concentrations, a sensor which could measure glucose, and other carbohydrates, under physiological conditions was developed. This sensor represents a particularly preferred embodiment of the present invention. The sensor was prepared as described above for the PEG-BA-PCCA, however instead of phenylboronic acid, 3-fluoro-4-aminophenylboronic acid was used as the molecular recognition component (referred to herein as PEG-BA2-PCCA). This sensor was tested for its ability to measure glucose concentrations under physiological conditions in an artificial tear fluid solution. The artificial tear fluid solution contained 2 mM tris-HCl, 150 NaCl, pH 7.5, 20 mM potassium chloride, 26 mM sodium bicarbonate, 5 mM urea, 3 mM ammonia, and albumin, globulin and lysozyme at a concentration of 8 g/L. This artificial tear fluid contains the most important components of tear fluid.

Figure 8:
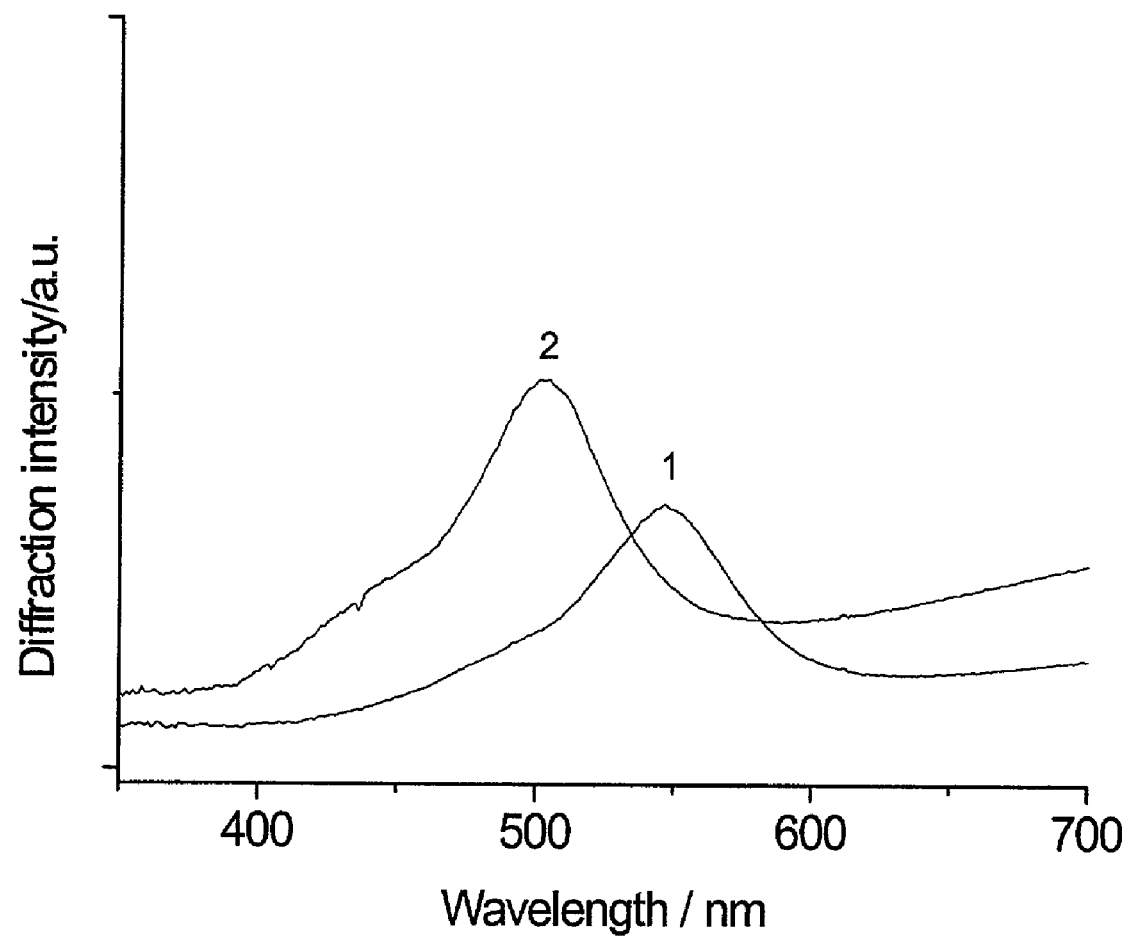
FIG. 8 shows the response of a PEG-BA-PCCA glucose sensor to (1) an absence of glucose and (2) the loading of 5 mM glucose to the solution, where the molecular recognition component of the sensor comprises 3-fluoro-4-aminophenylboronic acid and PEG, and where the original solution contained artificial tear fluid and was held at a pH of about 7.5, and where the blue shift in the diffraction response caused by the glucose loading was about 46 nm.

Referring now to FIG. 8, the PEG-BA2-PCCA of the present invention blue-shifted approximately 46 nm in the presence of 5 mM glucose in artificial tear fluid. In contrast, the BA-PCCA and PEG-BA-PCCA sensors described above did not show any significant diffraction shift in the presence of 5 mM glucose in this pH 7.5 artificial tear fluid. (Data not shown.)

Example 9

Formation and Use of GOD-PCCA Glucose Sensor

Figure 9:
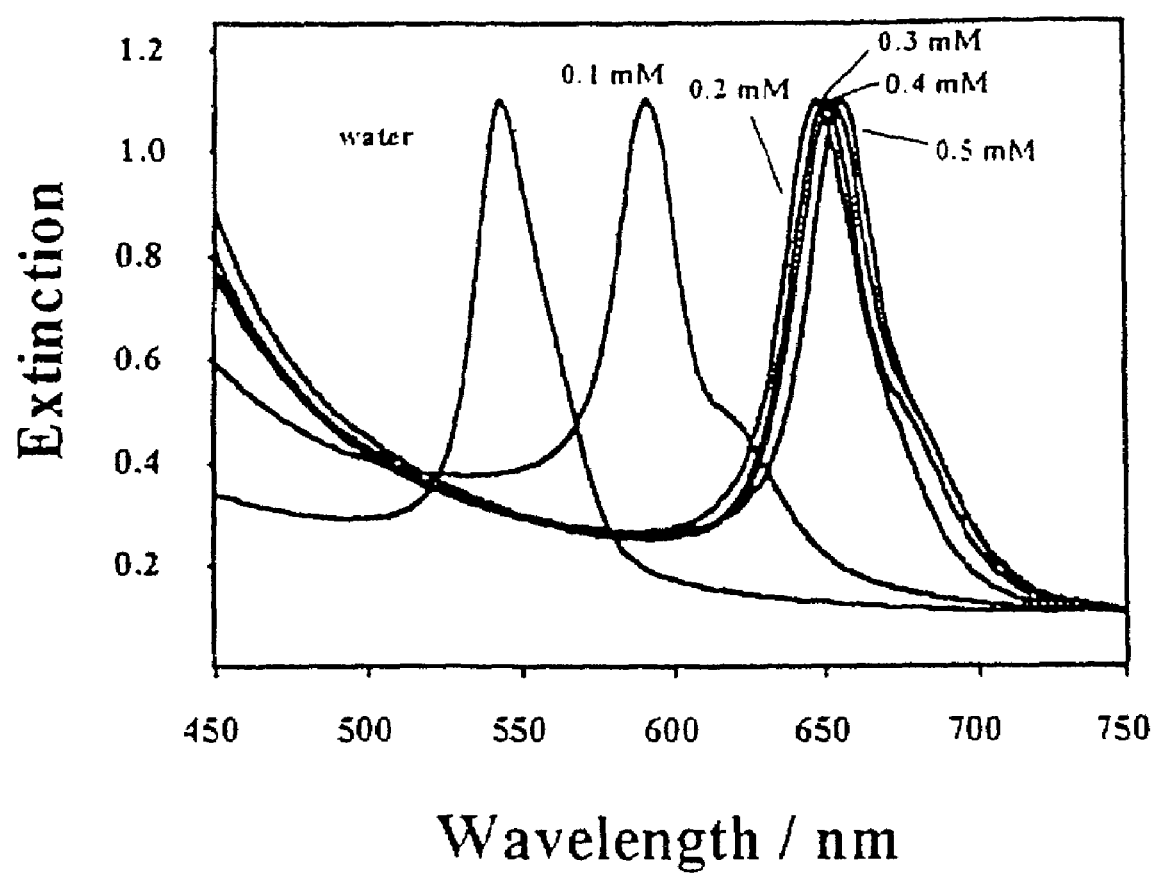
FIG. 9 shows the response of a PCCA glucose sensor in solutions having various concentrations of glucose, where glucose oxidase (GOD) is the molecular recognition component.

In the present Example, a glucose sensor device was prepared as described in the previous Examples, except that glucose oxidase (GOD) was used as the molecular recognition component that functionalized the PCCA. The GOD-PCCA glucose sensor was tested for detection of glucose in various glucose-containing solutions. As can be seen in FIG. 9, the diffraction wavelength when the GOD-PCCA glucose sensor was in water was approximately 550 nm. The diffracted wavelength shifted to about 600 nm in a solution of 0.1 mM glucose, and to about 650 nm in the 0.2 mM through 0.5 mM solutions of glucose. Reaction with the glucose by the GOD, when concentrations were at least 0.2 mM glucose, caused a wavelength shift of almost 100 nm, which corresponds to a color shift from yellowish green to deep red at normal incidence and which was easily seen with the unaided human eye.

Example 10

Detection of Dissolved Oxygen Using GOD-PCCA Glucose Sensor

Figure 10:
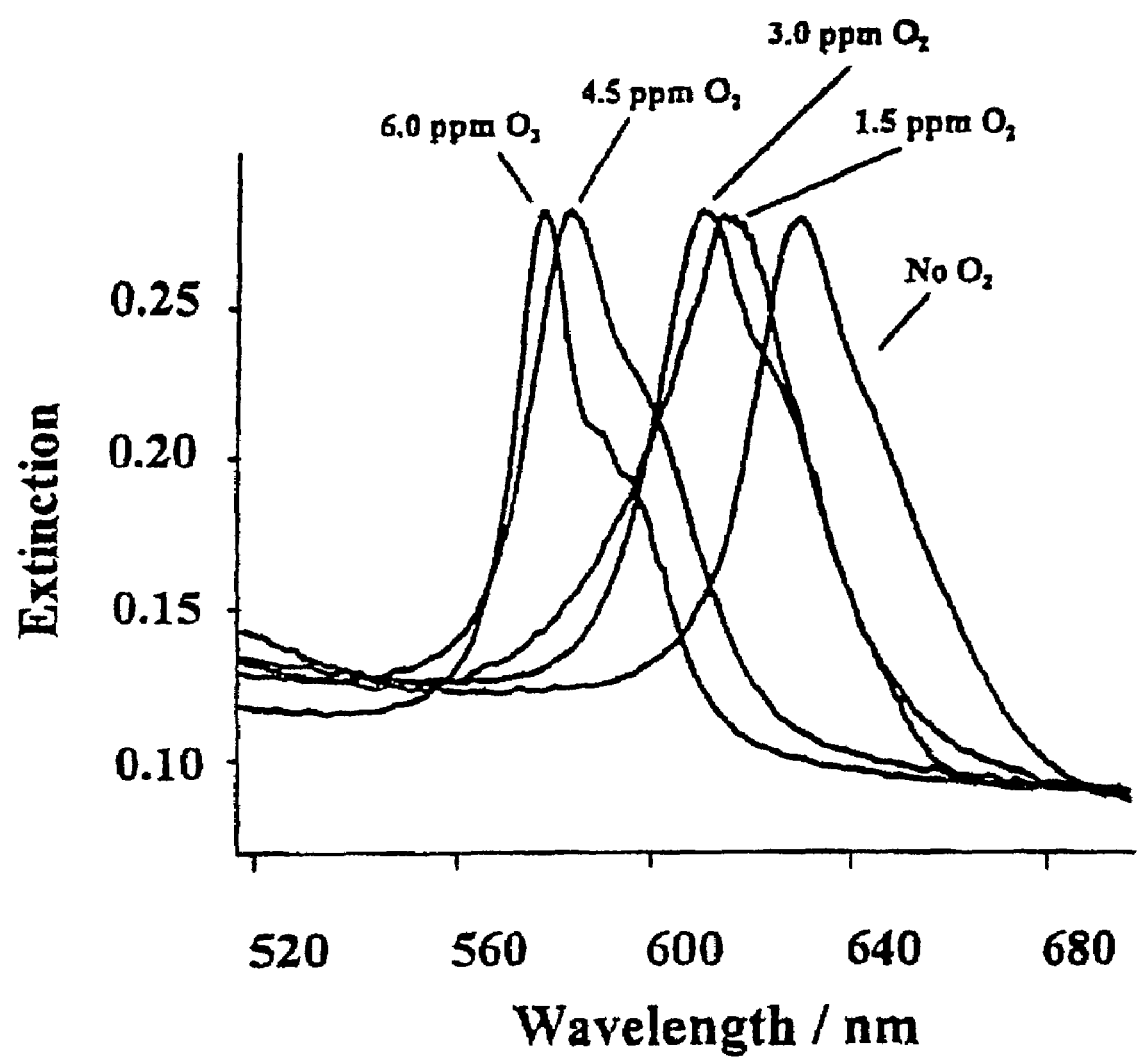
FIG. 10 shows the response of a PCCA glucose sensor in solutions having various concentrations of dissolved oxygen in the presence of a constant glucose concentration, where GOD is the molecular recognition component.

In the present Example, a GOD-PCCA glucose sensor was formed according to Example 9 above using GOD as the molecular recognition component. The glucose concentration was kept constant, at about 0.2 mM, to test the effects of dissolved oxygen on the GOD-PCCA glucose sensor. The results are presented in FIG. 10, which shows the dissolved oxygen dependence of the diffraction wavelength of the GOD-PCCA hydrogel. The GOD-PCCA glucose sensor was sensitive to oxygen levels between approximately 1.5 ppm and 6.0 ppm. Reoxidation of the flavin moiety on the GOD enzyme was believed to result in a shrinkage of the film. This demonstrated that the swelling of the glucose sensor was due to the anionic reduced form of the GOD and demonstrated the utility of the GOD-PCCA glucose sensor for detection of gases such as dissolved oxygen in solution. It should be noted that the glucose sensor using GOD as the molecular recognition component is not useful at physiological salinity levels.

What is claimed is:

1. A carbohydrate sensor comprising a polymerized crystalline colloidal array (PCCA) functionalized with a molecular recognition component capable of detecting said carbohydrate.

2. The sensor of claim 1, wherein the carbohydrate is glucose.

3. The sensor of claim 2, wherein the molecular recognition component is selected from the group consisting of glucose oxidase (GOD), dihydroxides of boron, barium, calcium, magnesium, and strontium, and boronic acid derivatives.

4. The sensor of claim 3, wherein the molecular recognition component is a boronic acid derivative selected from the group consisting of phenylboronic acid, p-nitrophenylboronic acid, 4-methoxyphenylboronic acid, α-naphthylboronic acid, 4-aminomethyl-2-N,N'-dimethylaminomethylphenylboronic acid, 3-fluoro-4-aminophenylboronic acid, and boronic acid derivatives having a $pK_a$ less than 7.

5. The sensor of claim 3, further comprising poly(ethylene)glycol or a crown ether.

6. The sensor of claim 1, wherein the polymerized crystalline colloidal array is polymerized in a hydrogel, and wherein the hydrogel undergoes a volume change in response to the carbohydrate.

7. The glucose sensor of claim 6, wherein the polymerized crystalline colloidal array has a lattice spacing that changes when said volume of said hydrogel changes, thereby causing the diffracted wavelength of the polymerized crystalline colloidal array to change.

8. A method for detecting the concentration of a carbohydrate in a solution comprising:
preparing a carbohydrate sensor comprising a crystalline colloidal array functionalized with a molecular recognition component capable of detecting the carbohydrate, wherein the crystalline colloidal array is polymerized in a hydrogel, wherein the hydrogel undergoes a volume change in response to the carbohydrate, and wherein said crystalline colloidal array has a lattice spacing that changes when the volume of the hydrogel changes, thereby causing the diffracted wavelength of the crystalline colloidal array to change;
contacting said polymerized crystalline colloidal array with said solution;
measuring the diffracted wavelength of said crystalline colloidal array before and after exposure to said solution; and
comparing the change in diffracted wavelength measurements before and after exposure to determine the concentration of the carbohydrate in said solution.

9. The method of claim 8, wherein said solution may be either a high ionic strength solution or a low ionic strength solution.

10. The method of claim 8, wherein said solution is blood, human tear fluid, artificial tear fluid, interstitial fluid, a fermentation solution, or another bodily fluid.

11. The method of claim 8, wherein the presence of the carbohydrate is determined by inspection of the diffracted wavelength by the polymerized crystalline colloidal array both before and after exposure to said solution, wherein the diffracted wavelength indicates concentration of the carbohydrate.

12. The method of claim 11, including employing the use of a detection device selected from the group consisting of a spectrometer or a spectrophotometer to determine said diffracted wavelength change.

13. The method of claim 11, including employing the unassisted human eye to determine said diffracted wavelength changes, wherein such a change is detectable by a change in color of the carbohydrate sensor.

14. The method of claim 8, wherein the carbohydrate is glucose.

15. The method of claim 8, wherein said carbohydrate sensor preparation step includes the steps of: allowing charged colloidal particles to self-assemble into a crystalline colloidal array;
(a) adding a first comonomer that is a gel monomer, a crosslinking agent, a molecular recognition component and a polymerization initiator to a medium comprising said crystalline colloidal array; and (b) polymerizing the mixture of step b) to form a crystalline colloidal array polymerized in a hydrogel.

16. The method of claim 8, wherein the molecular recognition component is selected from the group consisting of glucose oxidase (GOD), dihydroxides of boron, barium, calcium, magnesium, and strontium, and boronic acid derivatives.

17. The method of claim 16, wherein the molecular recognition component is a boronic acid derivative selected from the group consisting of phenylboronic acid, p-nitrophenylboronic acid, 4-methoxyphenylboronic acid, α-naphthylboronic acid, 4-aminomethyl-2-N,N'-dimethylaminomethylphenylboronic acid, 3-fluoro-4-aminophenylboronic acid, and boronic acid derivatives having a $pK_a$ less than 7.

18. The method of claim 16, further comprising adding poly(ethylene)glycol or a crown ether.

19. The method of claim 17, wherein the molecular recognition component comprises 3-fluoro-4-aminophenylboronic acid and poly(ethylene)glycol.

20. The method of claim 15, further comprising employing a gel selected from the group consisting of acrylamide gels, purified agarose gels, N-vinylpyrolidone gels, and methacrylate gels.

21. The method of claim 15, wherein the crosslinking agent is selected from the group consisting of N,N'-methylenebisacrylamide, methylenebismethacrylamide, and ethyleneglycol-dimethacrylate.

22. The method of claim 15, wherein the charged colloidal particles are selected from the group consisting of colloidal polystyrene, polymethylmethacrylate, silicon dioxide, aluminum oxide, polytetrafluoroethylene and poly N-isopropylacrylamide.

23. A contact lens comprising a carbohydrate sensor, which comprises a polymerized crystalline colloidal array (PCCA) functionalized with a molecular recognition component capable of detecting said carbohydrate.

24. The contact lens of claim 23, wherein said carbohydrate is glucose.

25. The contact lens of claim 23, wherein said molecular recognition component is selected from the group consisting of glucose oxidase (GOD), dihydroxides of boron, barium, calcium, magnesium, and strontium, and boronic acid derivatives.

26. The contact lens of claim 25, wherein the molecular recognition component is a boronic acid derivative selected from the group consisting of phenylboronic acid, p-nitrophenylboronic acid, 4-methoxyphenylboronic acid, α-naphthylboronic acid, 4-aminomethyl-2-N,N'-dimethylaminomethylphenylboronic acid, 3-fluoro-4-aminophenylboronic acid, and boronic acid derivatives having a $pK_a$ less than 7.

27. An optical insert comprising a carbohydrate sensor, which comprises a polymerized crystalline colloidal array (PCCA) functionalized with a molecular recognition component capable of detecting said carbohydrate.

28. The optical insert of claim 27, wherein said carbohydrate is glucose.

29. The optical insert of claim 28, wherein said insert may be inserted under the lower eyelid of a patient in order to determine the level of the carbohydrate in the tear fluid of the wearer of said optical insert.

30. The optical insert of claim 29, wherein the molecular recognition component is selected from the group consisting of glucose oxidase (GOD), dihydroxides of boron, barium, calcium, magnesium, and strontium, and boronic acid derivatives.

31. The optical insert of claim 30, wherein the molecular recognition component is a boronic acid derivative selected from the group consisting of phenylboronic acid, p-nitrophenylboronic acid, 4-methoxyphenylboronic acid, α-naphthylboronic acid, 4-aminomethyl-2-N,N'-dimethylaminomethylphenylboronic acid, 3-fluoro-4-aminophenylboronic acid, and boronic acid derivatives having a $pK_a$ less than 7.

32. The optical insert of claim 30, further comprising poly(ethylene)glycol or a crown ether.

33. A subcutaneous implant comprising a carbohydrate sensor, which comprises a biocompatible polymerized crystalline colloidal array (PCCA) functionalized with a molecular recognition component cable of detecting said carbohydrate.

34. The implant of claim 33, wherein said carbohydrate is glucose.

35. The implant of claim 34, wherein said molecular recognition component is selected from the group consisting of glucose oxidase (GOD), dihydroxides of boron, barium, calcium, magnesium, and strontium, and boronic acid derivatives.

36. The implant of claim 35, wherein the molecular recognition component is a boronic acid derivative selected from the group consisting of phenylboronic acid, p-nitrophenylboronic acid, 4-methoxyphenylboronic acid, α-naphthylboronic acid, 4-aminomethyl-2-N,N'-dimethylaminomethylphenylboronic acid, 3-fluoro-4-aminophenylboronic acid, and boronic acid derivatives having a $pK_a$ less than 7.

37. The implant of claim 35 further comprising poly(ethylene)glycol or a crown ether.

* * * * *